United States Patent [19]

Noelle et al.

[11] Patent Number: 5,747,037
[45] Date of Patent: May 5, 1998

[54] ANTI-GP39 ANTIBODIES

[75] Inventors: Randolph J. Noelle, Cornish, N.H.; Teresa M. Foy, Seattle, Wash.; Alejandro Aruffo, Edmonds, Wash.; Jeffrey A. Ledbetter, Seattle, Wash.

[73] Assignees: Bristol-Myers Squibb Company, New York, N.Y.; Trustees of Dartmouth College, Hanover, N.H.

[21] Appl. No.: 475,847

[22] Filed: Jun. 7, 1995

Related U.S. Application Data

[63] Continuation-in-part of Ser. No. 232,929, Apr. 25, 1994, abandoned, which is a continuation-in-part of Ser. No. 116,255, Sep. 2, 1993, abandoned.

[51] Int. Cl.$^6$ ................ A01K 39/395; C07K 16/28; C12N 5/12
[52] U.S. Cl. .................. 424/154.1; 424/130.1; 424/141.1; 424/143.1; 424/144.1; 424/153.1; 424/173.1; 435/70.11; 435/172.2; 435/326; 435/332; 435/334; 435/343; 435/343.1; 435/343.2; 435/346; 530/387.1; 530/388.1; 530/388.2; 530/388.22; 530/388.7; 530/388.73; 530/388.75
[58] Field of Search ................ 424/130.1, 141.1, 424/143.1, 153.1, 154.1; 530/387.1, 387.3, 388.22, 388.7, 388.75, 389.6; 435/172.2, 334, 343.2

[56] References Cited

U.S. PATENT DOCUMENTS 5,474,771 12/1995 Lederman et al. ............... 424/133.1

FOREIGN PATENT DOCUMENTS

| | | |
|---|---|---|
| 0 555 880 | 8/1993 | European Pat. Off. |
| 0 585 943 | 3/1994 | European Pat. Off. |
| WO 93/08207 | 4/1993 | WIPO |
| WO 93/09812 | 5/1993 | WIPO |

OTHER PUBLICATIONS

I. Paul (H2) Fumdamental Immunology 3rd Ed Raveu Press NY p. 242 only.

Foy, T.M. et al. (1993) "In Vivo CD40–gp39 Interactions are essential for Thymus–dependent Hummoral Immunity. II. Prolonged suppression of the Humoral Immune Response by an antibody to the ligand to CD40, gp39" *J. Exp Med.* 178:1567–1575.

Lederman, S. et al. (1992) "Identification of a novel surface protein on activated CD4$^+$ T Cells that induces contact–department B cell differentiation (Help)" *J. Exp. Med.* 175:1091–1101.

Lederman, S. et al. (1992) "Molecular Interactions Mediating T–B Lymphocyte Collaboration in Human Lymphoid Follicles" *J. Immnology* 149(12):3817–3826.

Marshall, L.S. et al. (1993) "The Molecular Basis for T Cell Help in Humoral Immunity: CD 40 and Its Ligand, gp39" *J. Clin. Immunol.* 13(3):165–174.

Noelle, R. and E.C. Snow (1992) "T helper cells" *Current Opinion in Immunology* 4:333–337.

Noelle, R.J. et al. (1992) "A 39–kDa protein on activated helper T cells binds CD40 and transduces the signal for cognate activation of B cells" *Proc Natl. Acad. Sci. USA* 89:6550–6554.

Noelle, R.J. et al. (1992) "CD40 and its ligand, an essential–ligand–receptor pair for thymus–dependent B–cell activation" *Immunology Today* 13:431–433.

*Primary Examiner*—Lila Feisee
*Assistant Examiner*—Phillip Gambel
*Attorney, Agent, or Firm*—Burns, Doane, Swecker & Mathis, LLP

[57] ABSTRACT

Antibodies that bind a protein gp39 (also referred to as CD40 ligand) are disclosed. Preferably, the antibodies are monoclonal antibodies of an IgG1 isotype and bind human gp39. In a preferred embodiment, an antibody of the invention binds an epitope recognized by a monoclonal antibody 24-31, produced by a hybridoma 24-31 (ATTC Accession No. HB11712) or binds an epitope recognized by a monoclonal antibody 89-76, produced by a hybridoma 89-76 (ATCC Accession No.HB11713). Pharmaceutical compositions comprising the antibodies of the invention are also disclosed. The antibodies of the invention are useful for inhibiting B cell proliferation and differentiation, T cell responses and for inducing T cell tolerance. Nucleic acid molecules encoding anti-gp39 antibodies, or portions thereof, as well as expression vectors and host cells incorporating said nucleic acid molecules, are also encompassed by the invention.

8 Claims, 16 Drawing Sheets

5,747,037

ANTI-GP39 ANTIBODIES

RELATED APPLICATIONS

This application is a Continuation-in-Part of U.S. patent application Ser. No. 08/232,929, abandoned, filed Apr. 25, 1994, and entitled "Methods for Inducing Antigen-specific T Cell Tolerance", which is a Continuation-in-Part of U.S. patent application Ser. No. 08/116,255 (abandoned in favor of U.S. Ser. No. 08/232,929), filed Sep. 2, 1993 entitled "Methods for Inducing Antigen-specific T Cell Tolerance", the entire contents of each of which are incorporated herein by reference.

GOVERNMENT FUNDING

The work leading to this invention may have been supported by one or more grants from the U.S. government. The U.S. government therefore may have certain rights in this invention.

BACKGROUND OF THE INVENTION

To induce antigen-specific T cell activation and clonal expansion, two signals provided by antigen-presenting cells (APCs) must be delivered to the surface of resting T lymphocytes (Jenkins, M. and Schwartz, R. (1987) *J. Exp. Med.* 165,302–319; Mueller, D. L., et al. (1990) *J. Immunol.* 144, 3701–3709; Williams, I. R. and Unanue, E. R. (1990) *J. Immunol.* 145, 85–93). The first signal, which confers specificity to the immune response, is mediated via the T cell receptor (TCR) following recognition of foreign antigenic peptide presented in the context of the major histocompatibility complex (MHC). The second signal, termed costimulation, induces T cells to proliferate and become functional (Schwartz, R. H. (1990) *Science* 248, 1349–1356). Costimulation is neither antigen-specific, nor MHC restricted and is thought to be provided by one or more distinct cell surface molecules expressed by APCs (Jenkins, M. K., et al. (1988) *J. Immunol.* 140, 3324–3330; Linsley, P. S., et al. (1991) *J. Exp. Med.* 173, 721–730; Gimmi, C. D., et al., (1991) *Proc. Natl. Acad. Sci. USA.* 88, 6575–6579; Young, J. W., et al. (1992) *J. Clin. Invest.* 90, 229–237; Koulova, L., et al. (1991) *J. Exp. Med.* 173, 759–762; Reiser, H., et al. (1992) *Proc. Natl. Acad. Sci. USA.* 89, 271–275; van-Seventer, G. A., et al. (1990) *J. Immunol.* 144, 4579–4586; LaSalle, J. M., et al., (1991) *J. Immunol.* 147, 774–80; Dustin, M. I., et al., (1989) *J. Exp. Med.* 169, 503; Armitage, R. J., et al. (1992) *Nature* 357, 80–82; Liu, Y., et al. (1992) *J. Exp. Med.* 175, 437–445). One costimulatory pathway involved in T cell activation involves the molecule CD28 on the surface of T cells. This molecule can receive a costimulatory signal delivered by a ligand on B cells or other APCs. Ligands for CD28 include members of the B7 family of B lymphocyte activation antigens, such as B7-1 and/or B7-2 (Freedman, A. S. et al. (1987) *J. Immunol.* 137, 3260–3267; Freeman, G. J. et al. (1989) *J. Immunol.* 143, 2714–2722; Freeman, G. J. et al. (1991) *J. Exp. Med.* 174, 625–631; Freeman, G. J. et al. (1993) *Science* 262, 909–911; Azuma, M. et al. (1993) *Nature* 366, 76–79; Freeman, G. J. et al. (1993) *J. Exp. Med.* 178, 2185–2192). B7-1 and B7-2 are also ligands for another molecule, CTLA4, present on the surface of activated T cells, although the role of CTLA4 in costimulation is unclear.

Delivery of an antigen-specific signal with a costimulatory signal to a T cell leads to T cell activation, which can include both T cell proliferation and cytokine secretion. In contrast, delivery of an antigen-specific signal to a T cell in the absence of a costimulatory signal is thought to induce a state of unresponsiveness or anergy in the T cell, thereby inducing antigen-specific tolerance in the T cell.

Interactions between T cells and B cells play a central role in immune responses. Induction of humoral immunity to thymus-dependent antigens requires "help" provided by T helper (hereafter Th) cells. While some help provided to B lymphocytes is mediated by soluble molecules released by Th cells (for instance lymphokines such as IL-4 and IL-5), activation of B cells also requires a contact-dependent interaction between B cells and Th cells. Hirohata et al., *J. Immunol.*, 140:3736–3744 (1988); Bartlett et al., *J. Immunol.*, 143:1745–1754 (1989). This indicates that B cell activation involves an obligatory interaction between cell surface molecules on B cells and Th cells. The molecule(s) on the T cell therefore mediates contact-dependent helper effector functions of T cells. A contact-dependent interaction between molecules on B cells and T cells is further supported by the observation that isolated plasma membranes of activated T cells can provide helper functions necessary for B cell activation. Brian, *Proc. Natl. Acad. Sci. USA*, 85:564–568 (1988); Hodgkin et al., *J. Immunol.*, 145:2025–2034 (1990); Noelle et al., *J. Immunol.*, 146:1118–1124 (1991).

A molecule, CD40, has been identified on the surface of immature and mature B lymphocytes which, when crosslinked by antibodies, induces B cell proliferation. Valle et al., *Eur. J Immunol.*, 19:1463–1467 (1989); Gordon et al., *J. Immunol.*, 140:1425–1430 (1988); Gruber et al., *J. Immunol.*, 142:4144–4152 (1989). CD40 has been molecularly cloned and characterized. Stamenkovic et al., *EMBO J.*, 8:1403–1410 (1989). A ligand for CD40, gp39 (also called CD40 ligand or CD40L) has also been molecularly cloned and characterized. Armitage et al., *Nature*, 357:80–82 (1992); Lederman et al., *J. Exp. Med.*, 175:1091–1101 (1992); Hollenbaugh et al., *EMBO J.*, 11:4313–4319 (1992). The gp39 protein is expressed on activated, but not resting, CD4+ Th cells. Spriggs et al., *J. Exp. Med.*, 176:1543–1550 (1992); Lane et al., *Eur. J. Immunol.*, 22:2573–2578 (1992); Roy et al., *J. Immunol.*, 151:1–14 (1993). Cells transfected with the gp39 gene and expressing the gp39 protein on their surface can trigger B cell proliferation and, together with other stimulatory signals, can induce antibody production. Armitage et al., *Nature*, 357:80–82 (1992); Hollenbaugh et al., *EMBO J.*, 11:4313–4319 (1992).

SUMMARY OF THE INVENTION

Cell-surface molecules which mediate contact-dependent helper effector functions of T cells are important for inducing immune responses which require T cell help. For example, the interaction of gp39 on T cells with CD40 on B cells plays a central role in activating B cell responses to antigens. The current invention is based, at least in part, on the discovery that cell-surface molecules which mediate contact-dependent helper effector functions also play a critical role in the response of T cells to antigens. In particular, it has been discovered that, under appropriate conditions, interference of an interaction between gp39 on a T cell and a ligand on a cell which is presenting antigen to the T cell can induce antigen-specific T cell tolerance. Accordingly, the cell which presents antigen to the T cell requires an interaction between a gp39 ligand (e.g., CD40) on the cell and gp39 on the T cell to be able to provide signals necessary for activation of the T cell. Inhibition of the interaction between the gp39 ligand and gp39 prevents T cell activation and rather induces antigen-specific T cell tolerance.

The methods of the invention pertain to induction of antigen-specific T cell tolerance. The methods involve contacting a T cell with: 1) a cell which presents antigen to the T cell and has a ligand on the cell surface which interacts with a receptor on the surface of the T cell which mediates contact-dependent helper effector functions; and 2) an antagonist of the receptor on the surface of a T cell which mediates contact-dependent helper effector functions. The antagonist inhibits the interaction of the receptor with it's ligand. A T cell can be contacted with the cell which presents antigen and the antagonist in vitro, or alternatively, the cell and the antagonist can be administered to a subject to induce T cell tolerance in vivo.

In a preferred embodiment, the receptor on the surface of the T cell which mediates contact-dependent helper effector functions is gp39. In this embodiment, the antagonist is a molecule which inhibits the interaction of gp39 with its ligand on a cell which presents antigen to the T cell. A particularly preferred gp39 antagonist is an anti-gp39 antibody. Alternatively, the gp39 antagonist is a soluble form of a gp39 ligand, for example soluble CD40. The cell which presents antigen to a T cell is preferably a B cell. The B cell can be a small, resting B cell. To induce T cell tolerance to a soluble antigen, the B cell can be contacted with the antigen prior to contact with the T cell (e.g., prior to administration to a subject). In another embodiment, to induce T cell tolerance to alloantigens, the cell which is used to present antigen to the T cell is an allogeneic cell. The allogeneic cell can be, for example, an allogeneic B cell, allogeneic bone marrow, allogeneic spleen cells or allogeneic cells in peripheral blood.

The methods of the current invention can be used, for example, to induce T cell tolerance to a soluble antigen, to induce T cell tolerance a bone marrow transplant or other organ transplant or to inhibit graft-versus-host disease in bone marrow transplantation. In the case of bone marrow transplantation, the transplanted bone marrow cells themselves serve as cells which present antigen to the T cell in the method of the invention. Accordingly, in one embodiment of the invention, acceptance of a bone marrow transplant is promoted by administering to a subject allogeneic bone marrow in conjunction with a gp39 antagonist (e.g., an anti-gp39 antibody).

This invention further pertains to anti-human gp39 monoclonal antibodies capable of inhibiting B cell proliferation, B cell differentiation and T cell responses and to pharmacuetical compositions comprising such antibodies. Anti-human gp39 monoclonal antibodies of the invention are preferred for use in modulating immune responses in general, and particularly for use in inducing antigen-specific T cell tolerance. Preferred antibodies include monoclonal antibodies 3E4, 2H5, 2H8, 4D9-8, 4D9-9, 24-31, 24-43, 89-76 and 89-79, described in Example 6. Particularly preferred antibodies are monoclonal antibodies 89-76 and 24-31. The 89-76 and 24-31 hybridomas, producing the 89-76 and 24-31 antibodies, respectively, were deposited under the provisions of the Budapest Treaty with the American Type Culture Collection, Parklawn Drive, Rockville, Md., on Sep. 2, 1994. The 89-76 hybridoma was assigned ATCC Accession Number HB11713 and the 24-31 hybridoma was assigned ATCC Accession Number HB11712. The 24-31 and 89-76 antibodies are of the IgG1 isotype.

Accordingly, in one embodiment, the invention provides an anti-human gp39 monoclonal antibody (mAb) of an IgG1 isotype. The anti-human gp39 mAb of the invention can inhibit B cell proliferation in a standard in vitro assay, for example, B cell proliferation induced by treatment of the B cells with interleukin-4 and soluble gp39. Preferably, the anti-human gp39 antibody inhibits B cell proliferation with an $IC_{50}$ (i.e., concentration necessary to inhibit proliferation by 50%) between about 0.01 and 5.0 µg/ml, more preferably between about 0.1 and 2.5 µg/ml, and even more preferably between about 0.1 and 1.25 µg/ml. The anti-human gp39 mAbs of the invention can also inhibit B cell production of IgG, IgM and/or IgA in a standard in vitro assay, for example, Ig production induced by culturing of B cells with activated T cells (e.g., T cells activated by treatment with anti-CD3 antibody). Preferably, the anti-human gp39 antibody inhibits B cell production of IgG, IgM and/or IgA with an IC50 between about 0.01 and 1.0 µg/ml or, more preferably, between about 0.01 and 0.1 µg/ml.

In a preferred embodiment, the anti-human gp39 mAb of the invention binds an epitope recognized by a monoclonal antibody selected from a group consisting of 3E4, 2H5, 2H8, 4D9-8, 4D9-9, 24-31, 24-43, 89-76 and 89-79. More preferably, the anti-human gp39 mAb binds an epitope recognized by monoclonal antibody 24-31 or monoclonal antibody 89-76. The ability of an mAb to bind an epitope recognized by any of the aforementioned antibodies can be determined by standard cross-competition assays. For example, an antibody that binds the same epitope recognized by mAb 24-31 will compete for the binding of labeled 24-31 to activated T cells, whereas an antibody that binds a different epitope than that recognized by mAb 24-31 will not compete for the binding of labeled 24-31 to activated T cells.

The invention also provides pharmaceutical compositions of the anti-human gp39 antibodies of the invention. These compositions typically comprise an anti-human gp39 mAb (e.g., preferably 24-31 or 89-76) and a pharmaceutically acceptable carrier.

Yet another aspect of the invention pertains to nucleic acid encoding an anti-human gp39 mAb (e.g., DNA encoding an immunoglobulin heavy chain or light chain, or portion thereof, of an anti-human gp39 mAb). Such nucleic acid can be isolated from a cell (e.g., hybridoma) producing an anti-human gp39 mAb by standard techniques. For example, nucleic acid encoding the 24-31 or 89-76 mAb can be isolated from the 24-31 or 89-76 hybridoma, respectively, by cDNA library screening, PCR amplification or other standard technique. Nucleic acid encoding an anti-human gp39 mAb chain can be manipulated by standard recombinant DNA techniques to produce recombinant anti-human gp39 mAbs, for example, chimeric or humanized anti-human gp39 mAbs.

Moreover, nucleic acid encoding an anti-human gp39 mAb can be incorporated into an expression vector and introduced into a host cell to facilitate expression and production of recombinant forms of anti-human gp39 antibodies.

Figure 3A:
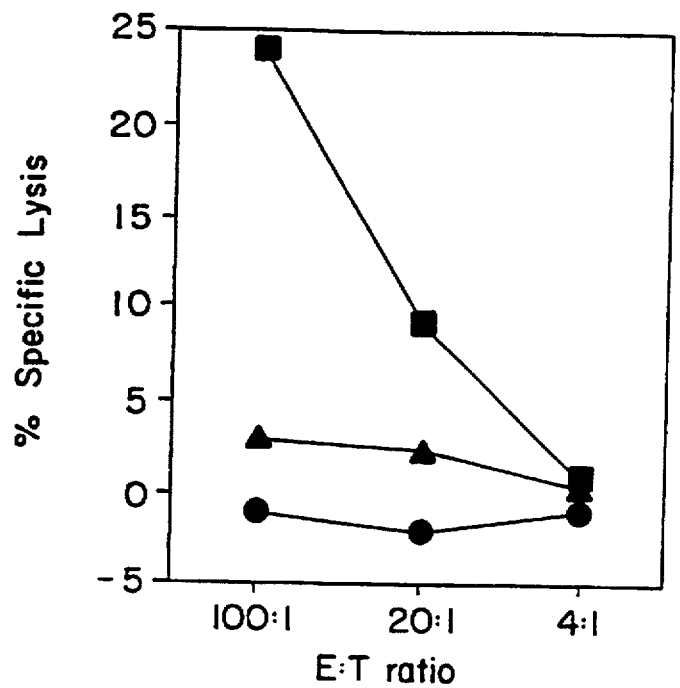
FIG. 3A is a graphic representation of the inhibition of primary allogeneic CTL responses induced by allogeneic B cells when recipient animals are treated with anti-gp39 antibody. Groups represented are untreated mice (■), anti-gp39 treated mice (Δ) and spleen cells from unprimed Balb/c mice (●; used as negative control effector cells).
Figure 3B:
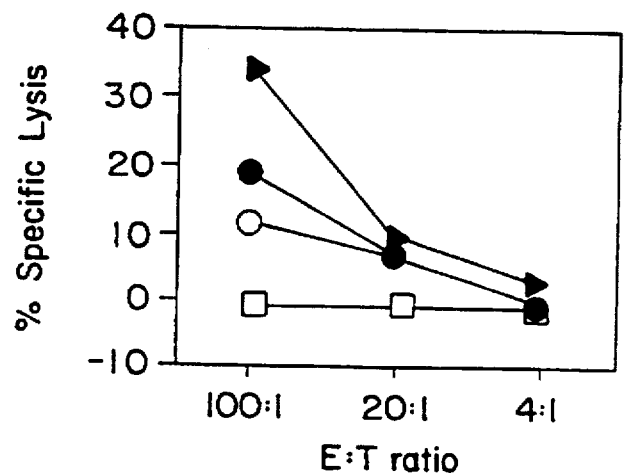
Figure 3C:
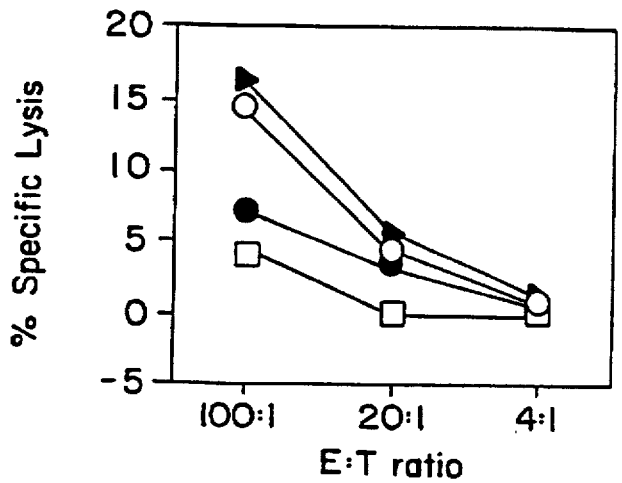

FIGS. 3B and 3C are graphic representations of the inhibition of primary allogeneic CTL responses induced by LPS-treated B cell blasts when recipient animals are treated with anti-gp39 antibody. Panels B and C represent two independent experiments. Groups represented are LPS blasts in vivo without treatment (>), LPS blasts in vivo with anti-gp39 treatment (●), resting B cells in vivo without treatment (○) and resting B cells in vivo with anti-gp39 treatment (□).

Figure 4A:
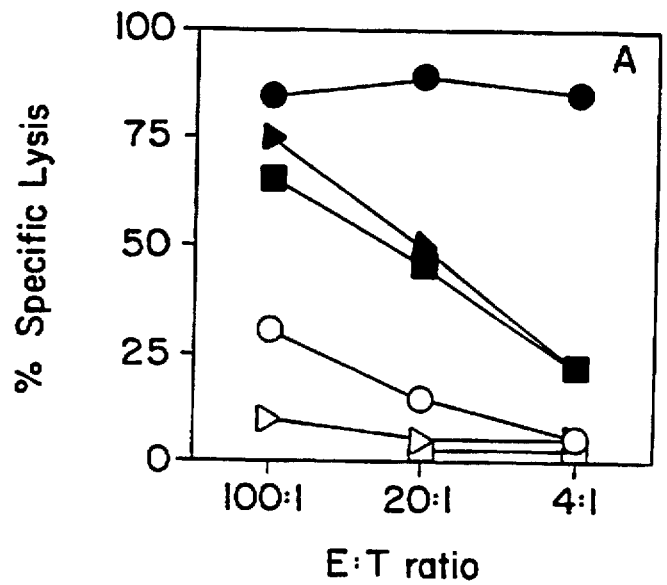

FIG. 4A is a graphic representation of the inhibition of secondary allogeneic CTL responses induced by allogeneic B cells when recipient animals are treated with anti-gp39 antibody. Effector groups shown are: HIg treated recipients (●), naive Balb/c (>) and anti-gp39 treated recipients (■). Corresponding syngeneic response (Balb/c cells stimulated with Balb/c cells) are indicated by open symbols.

Figure 4B:
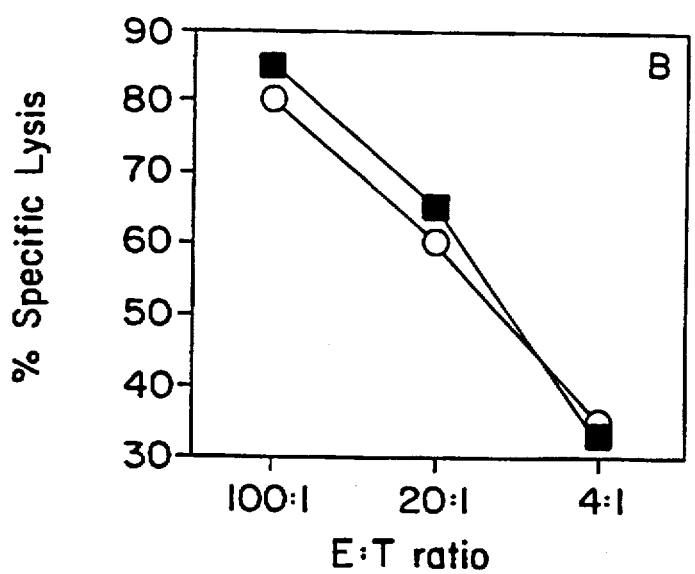

FIG. 4B is a graphic representation of the specificity of inhibition of allogeneic CTL responses by anti-gp39 treatment. Shown are CTL responses against $H-2^k$ targets by naive Balb/c cells (○) or by cells tolerized to $H-2^b$ by administration of $H-2^b$ haplotype B cells and anti-gp39 (■).

Figure 5:
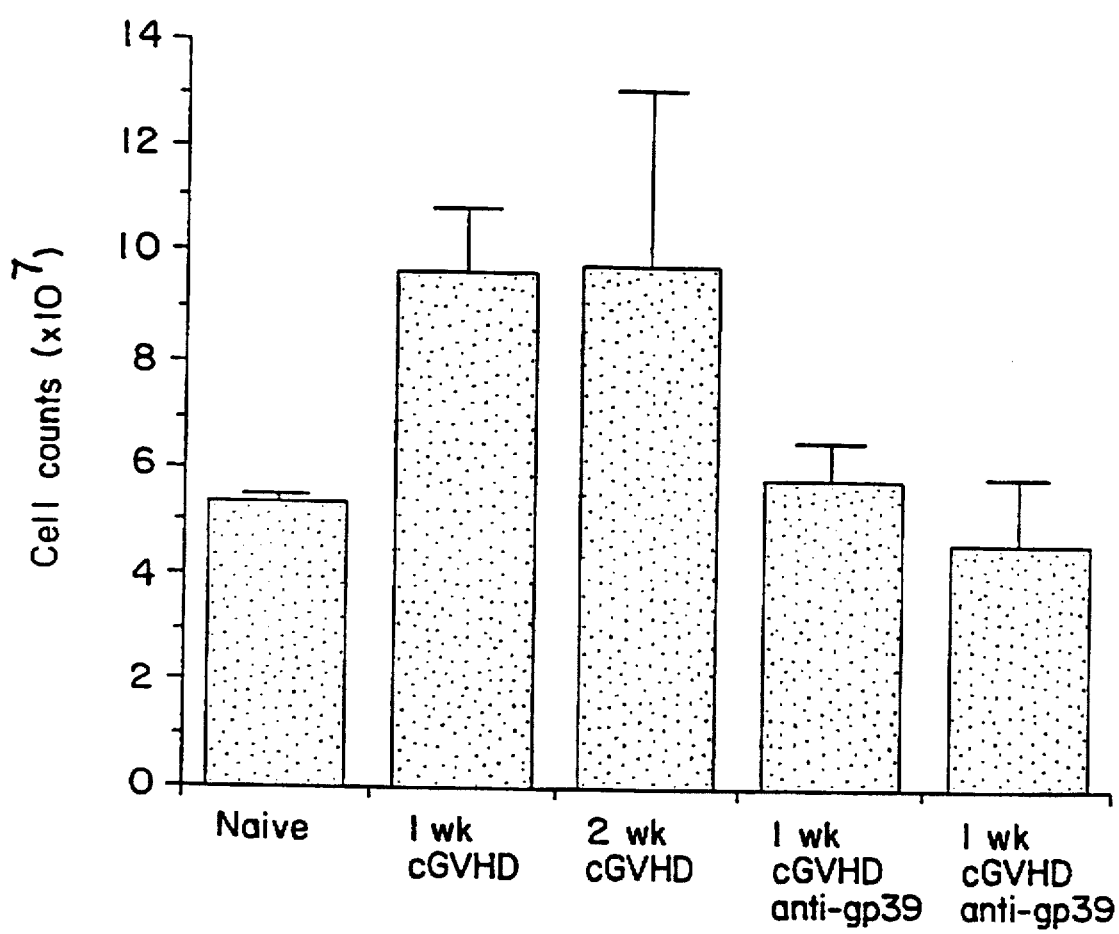

FIG. 5 is a bar graph depicting the number of splenocytes in a host which has received a bone marrow transplant at various times after transfer of the bone marrow to the host either with or without treatment with an anti-gp39 antibody.

Figure 6A:
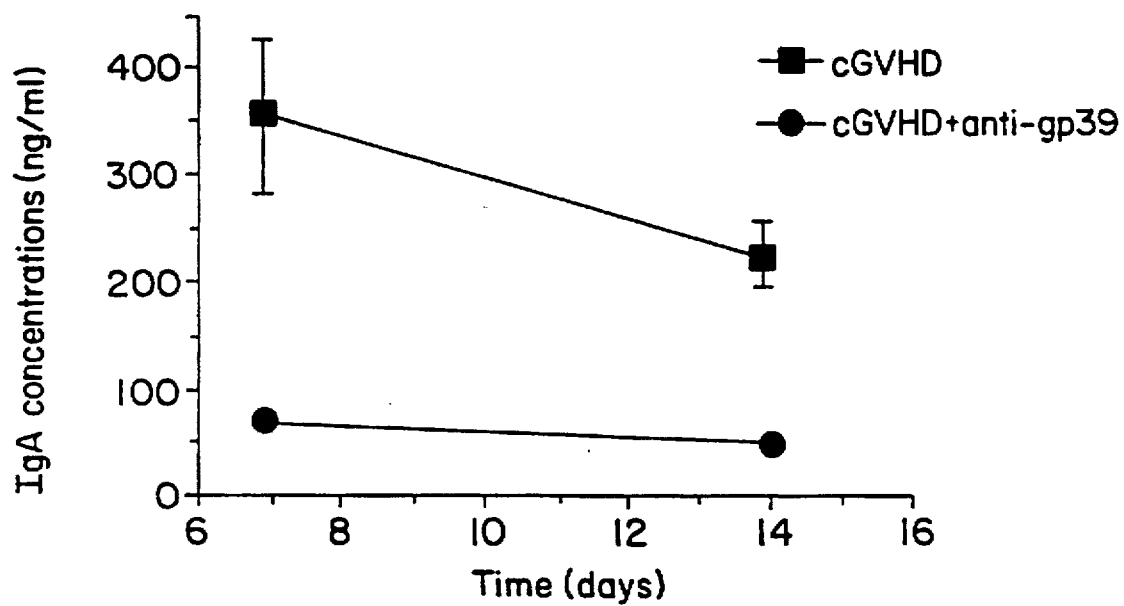

FIG. 6A is a graphic representation of the concentration of IgA produced by splenic B cells in vitro after removal from mice which received a bone marrow transplant either with or without in vivo anti-gp39 treatment. Splenic B cells were removed and antibody production measured either 7 or 14 days after bone marrow transplantation.

Figure 6B:
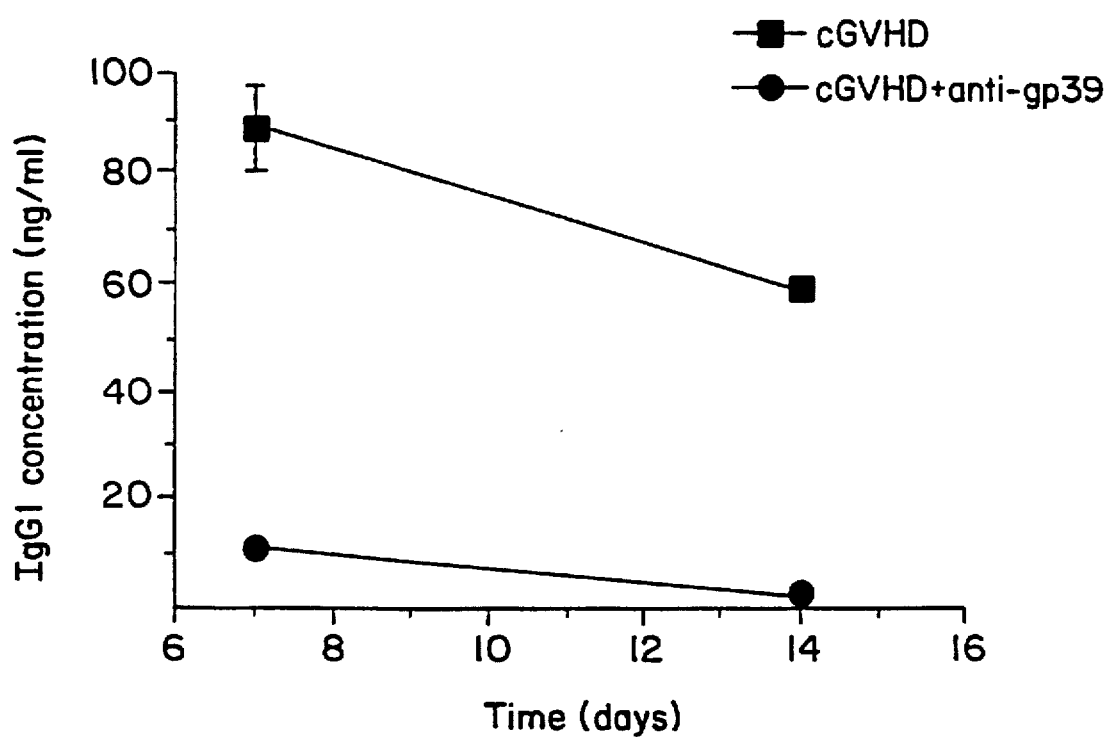

FIG. 6B is a graphic representation of the concentration of IgG1 produced by splenic B cells in vitro after removal from mice which received a bone marrow transplant either with or without in vivo anti-gp39 treatment. Splenic B cells were removed and antibody production measured either 7 or 14 days after bone marrow transplantation.

Figure 7A:
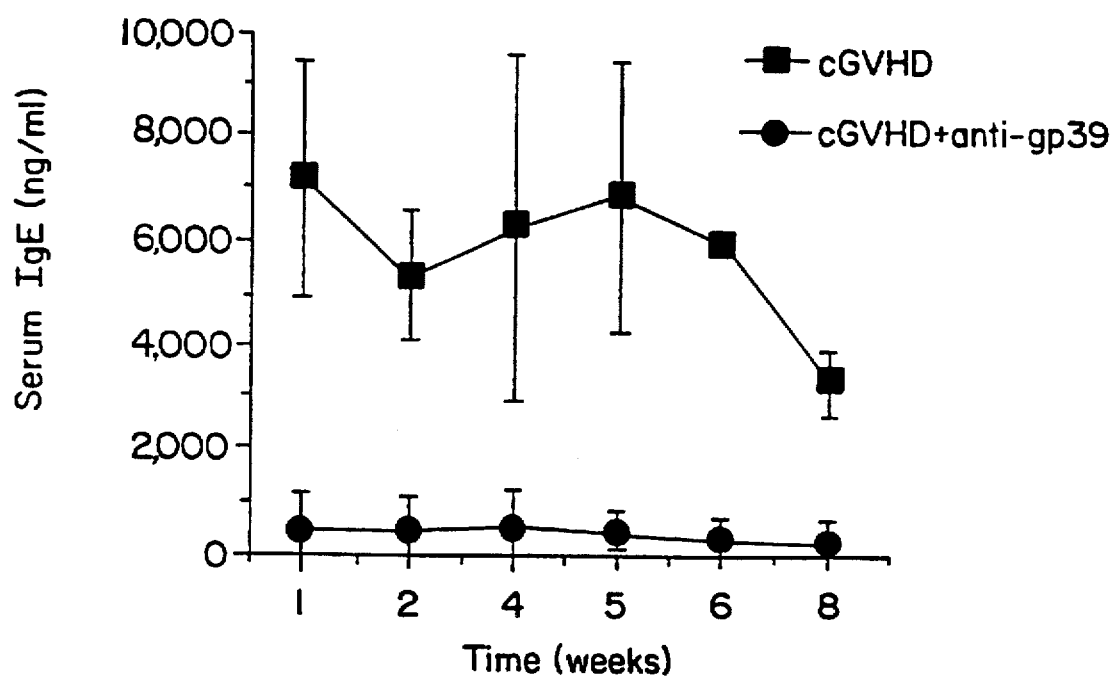

FIG. 7A is a graphic representation of the serum IgE concentrations in mice which received a bone marrow transplant either with or without in vivo anti-gp39 treatment at various times after bone marrow transfer.

Figure 7B:
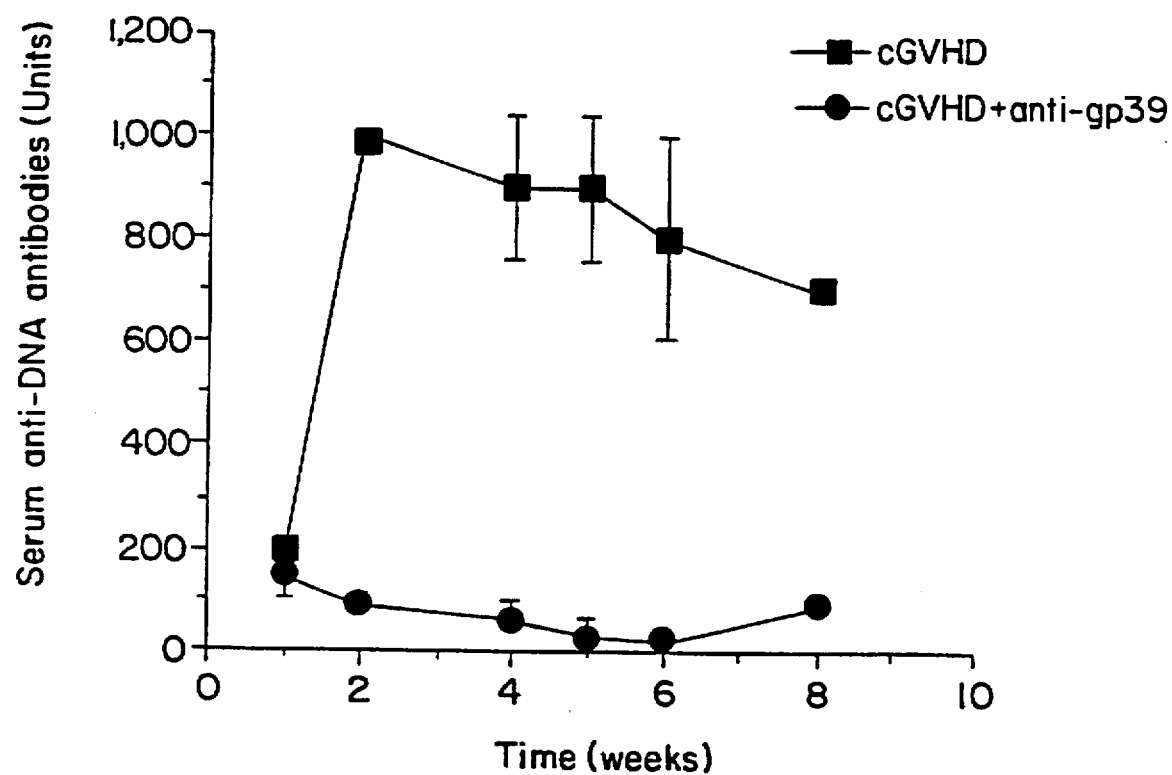

FIG. 7B is a graphic representation of the serum anti-DNA antibody concentrations in mice which received a bone marrow transplant either with or without in vivo anti-gp39 treatment at various times after bone marrow transfer.

Figure 8A:
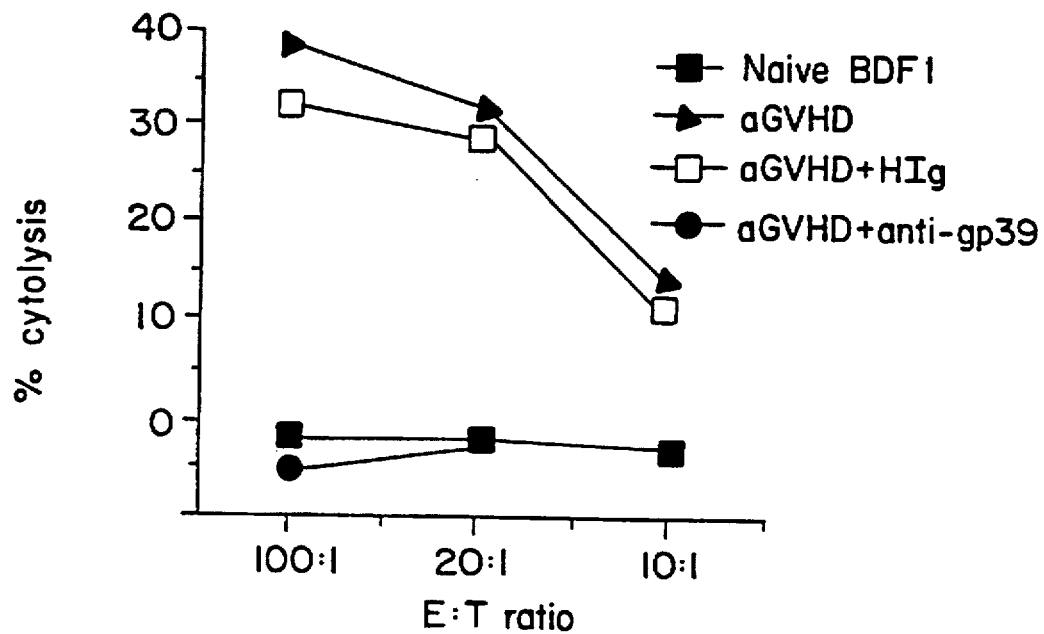
Figure 8B:
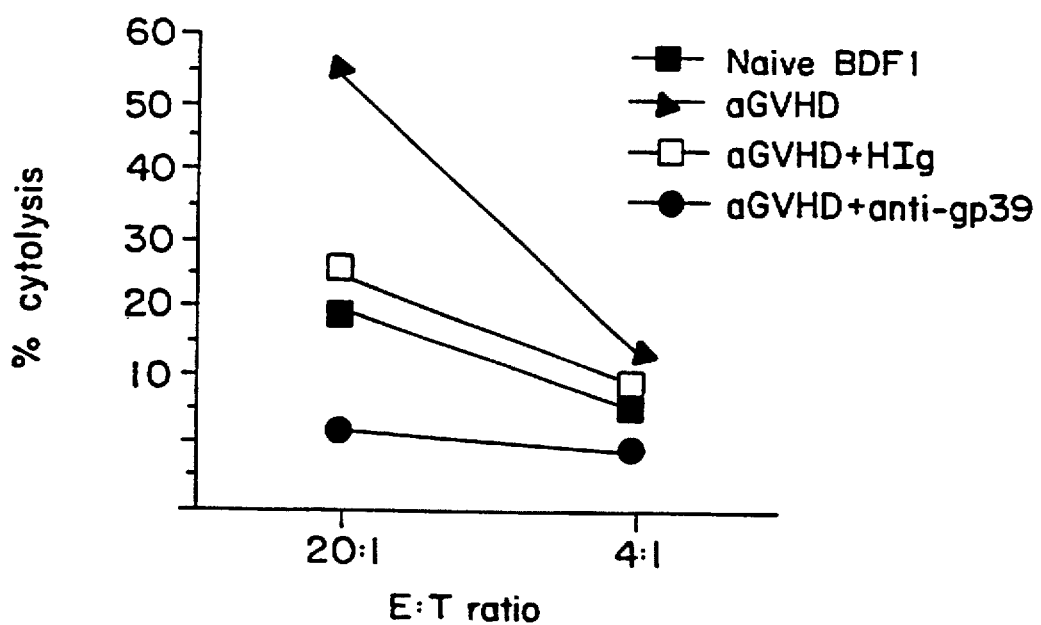

FIGS. 8A and 8B are graphic representations depicting the cytolytic activity in vitro of cytotoxic T cells from mice which received a bone marrow transplant either with or without in vivo anti-gp39 treatment at different effector to target cell ratios (E:T ratio). Panels A and B represent two independent experiments.

Figure 9A:
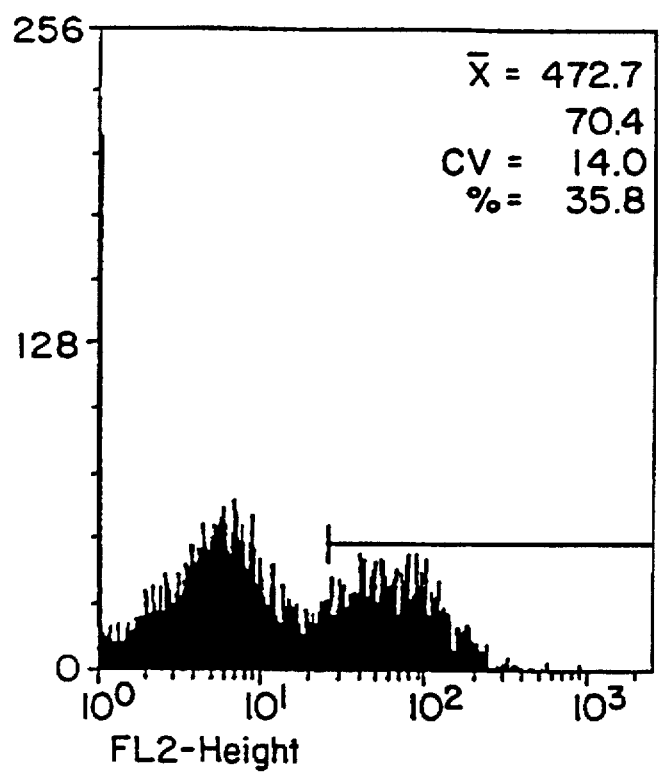
Figure 9B:
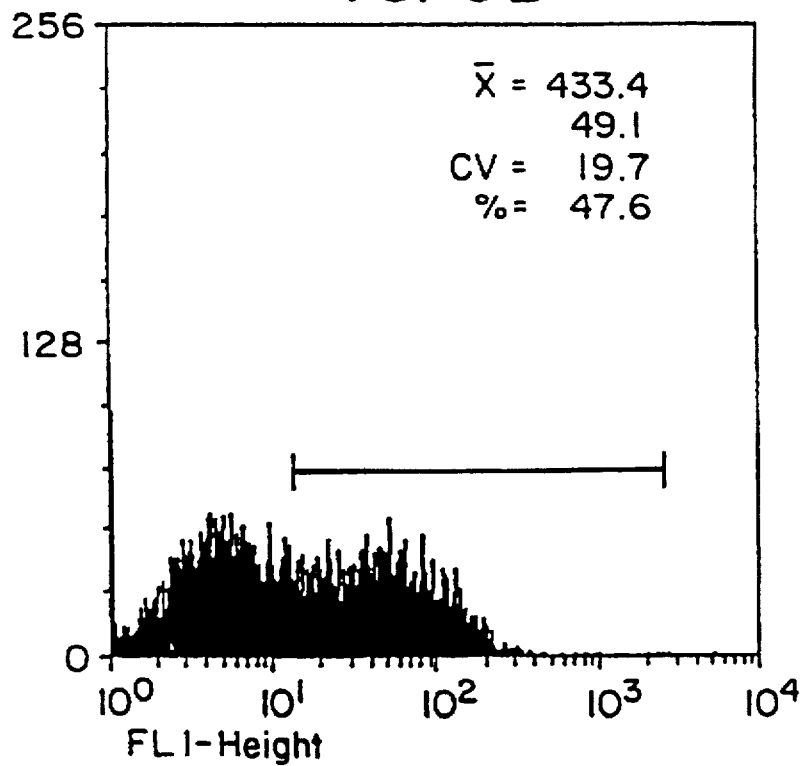
Figure 9C:
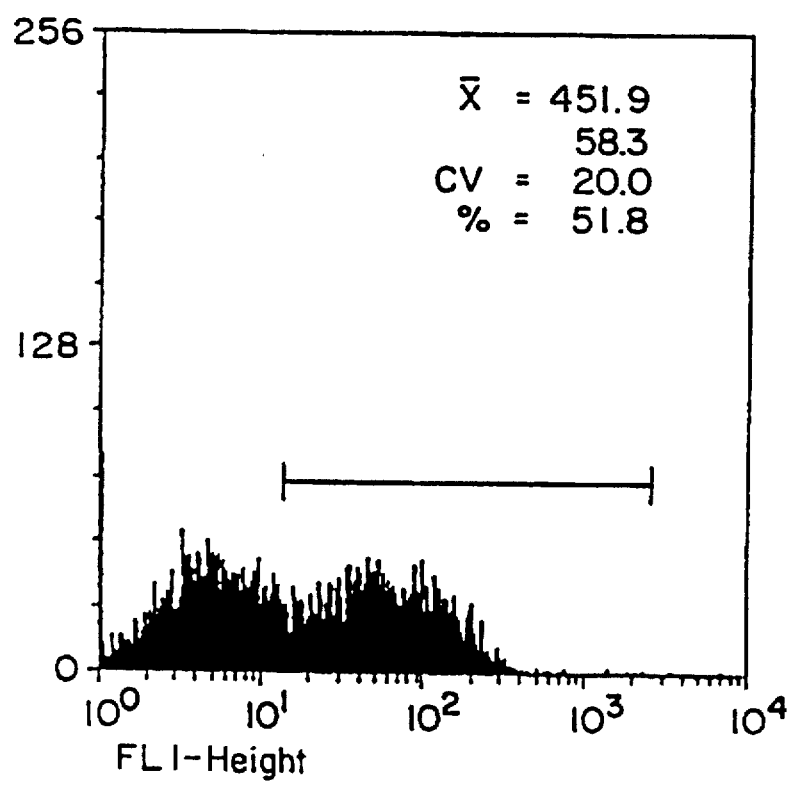

FIGS. 9A, 9B and 9C are flow cytometic profiles depicting the staining of 6 hour activated human peripheral blood lymphocytes with either CD40Ig (panel A), mAb 4D9-8 (panel B) or mAb 4D9-9 (panel C).

Figure 10A:
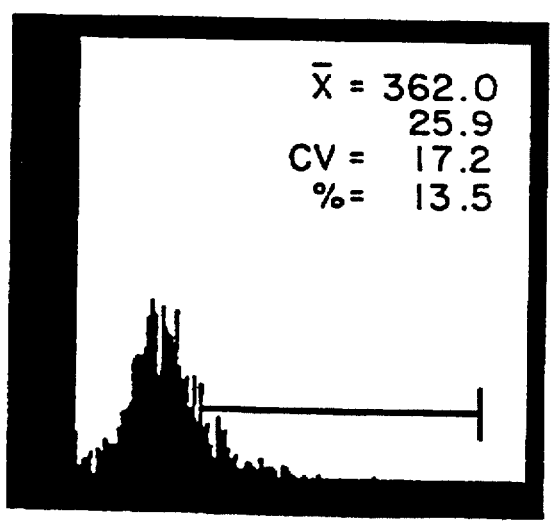
Figure 10B:
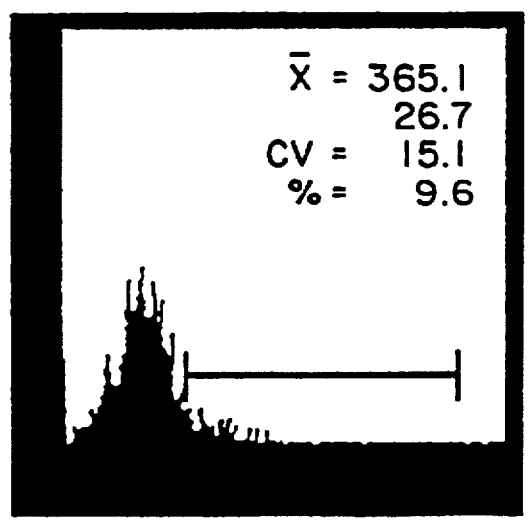
Figure 10C:
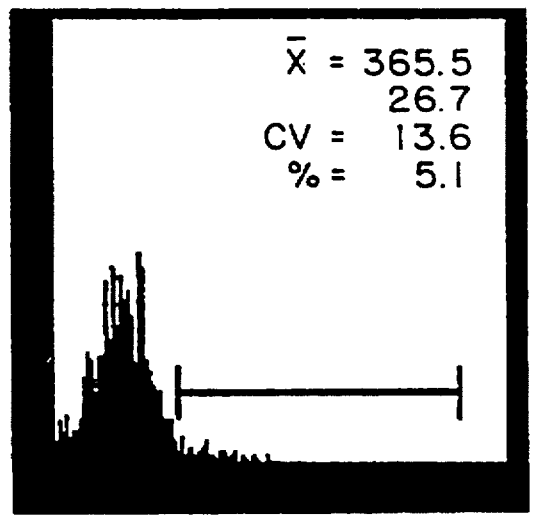

FIGS. 10A, 10B and 10C are flow cytometic profiles depicting the staining of 6 hour activated human peripheral blood lymphocytes cultured in the presence of cycloporin A stained with either mAb 4D9-8 (panel A), mAb 4D9-9 (panel B) or CD40Ig (panel C).

Figure 11A:
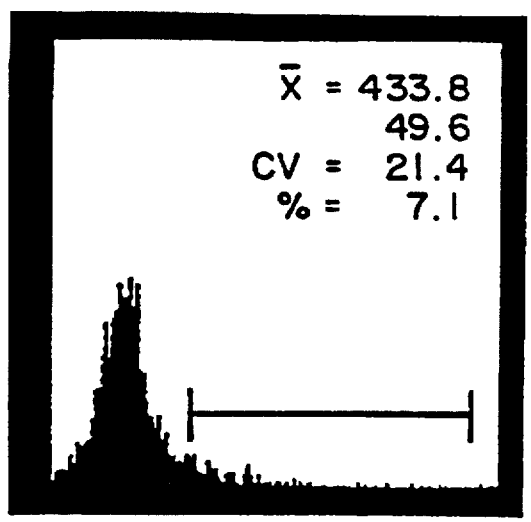
Figure 11B:
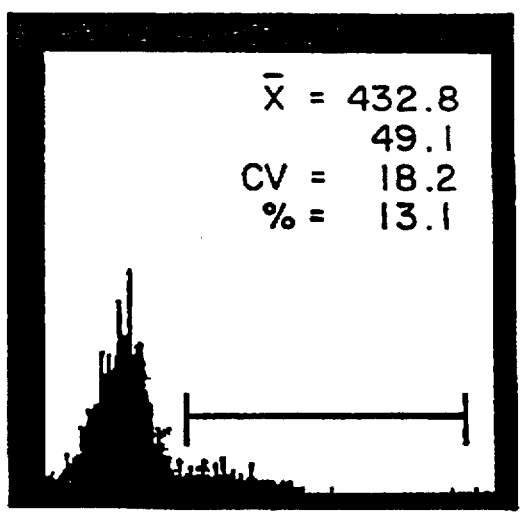

FIGS. 11A and 11B are flow cytometric profiles depicting the staining of 6 hour activated human peripheral blood lymphocytes with CD40Ig in the presence of unlabeled mAb 4D9-8 (panel A) or unlabeled mAb 4D9-9 (panel B).

Figure 12:
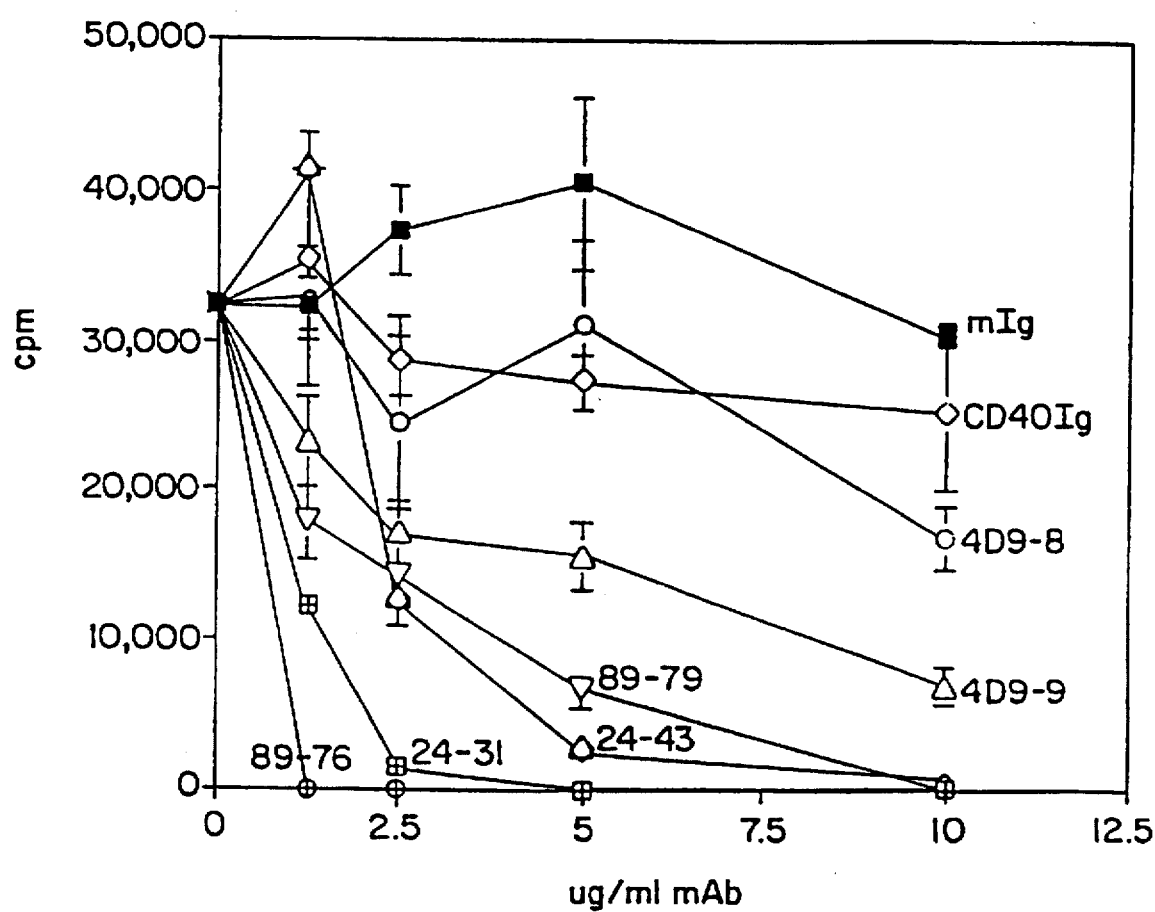

FIG. 12 is a graphic representation of the inhibition of human B cell proliferation induced by soluble gp39 and IL-4 when cells are cultured in the presence of anti-human gp39 mAbs 4D9-8, 4D9-9, 24-31, 24-43, 89-76 or 89-79.

Figure 13:
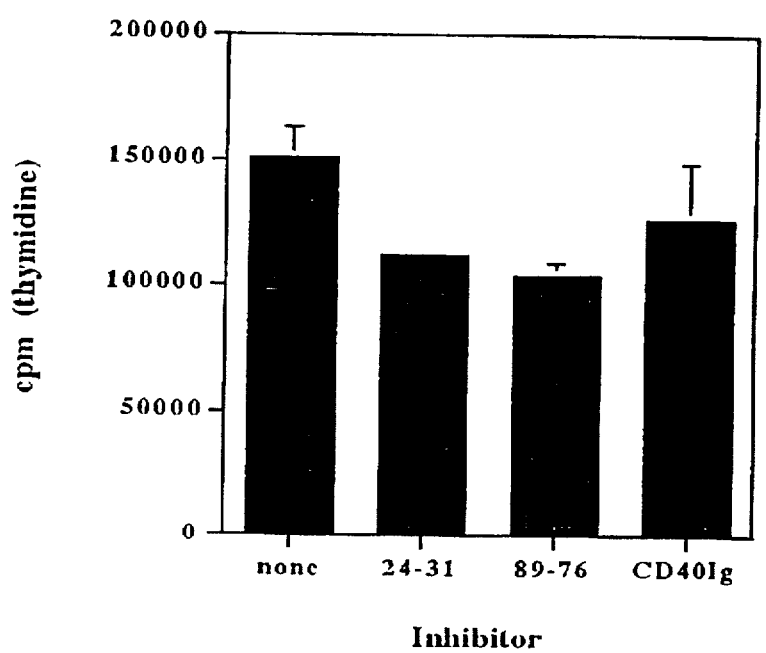

FIG. 13 is a histogram representing the results of a proliferation assay of TT specific T cells from TT immunized hu-PBL-scid mice performed in the absence of inhibitor (none) or in the presence of anti-human gp39 antibody 24-31 or 89-76, or CD40Ig.

DETAILED DESCRIPTION OF THE INVENTION

This invention features methods for inducing antigen-specific T cell tolerance. The methods involve contacting a T cell with 1) a cell which presents antigen to the T cell and has a ligand on the cell surface that interacts with a receptor on the surface of the T cell which mediates contact dependent helper effector functions, and 2) an antagonist of the receptor on the T cell which inhibits interaction of the receptor an the ligand. As defined herein, a molecule or receptor which mediates contact dependent helper effector functions is one which is expressed on a Th cell and interacts with a ligand on an effector cell (e.g., a B cell), wherein the interaction of the receptor with its ligand is necessary for generation of an effector cell response (e.g., B cell activation). In addition to being involved in effector cell responses, it has now been found that such a molecule is involved in the response of the T cell to antigen.

A preferred molecule on a T cell which mediates contact-dependent helper effector function is gp39. Accordingly, in preferred embodiments, the methods of the invention involve contacting a T cell with a cell which presents antigen and a gp39 antagonist. Accordingly, the cell used to present antigen is one which interacts with gp39 on the surface of a T cell to activate the T cell (i.e. deliver the necessary signals for T cell activation to the T cell). For example, the cell can be a B cell which expresses CD40 and presents antigen to the T cell. By inhibiting an interaction between a gp39 ligand on the cell presenting antigen with gp39 on the T cell, the T cell is not activated by the presented antigen but rather becomes tolerized to the antigen.

The methods of the invention can be used to induce T cell tolerance to an antigen in vivo. For example, a cell which presents antigen to a T cell can be administered to a subject in conjunction with an antagonist of a receptor expressed on the T cell which mediates contact dependent helper effector function (e.g. a gp39 antagonist). The methods of the invention can further be used to tolerize a T cell to an antigen in vitro by contacting the T cell in vitro with a cell which presents antigen to the T cell together with an antagonist of a receptor expressed on the T cell which mediates contact dependent helper effector function (e.g. a gp39 antagonist). T cells tolerized in vitro can then be administered to a subject. The methods of the invention can be used to tolerize T cells in a subject to a specific antigen, or to transplanted cells, such as allogeneic bone marrow (e.g., in bone marrow transplantation). The methods of the invention are also useful for inhibiting graft versus host disease in bone marrow transplantation.

Various aspects of the invention are described in further detail in the following subsections.

I. gp39 Antagonists

According to the methods of the invention, a gp39 antagonist is contacted with a T cell (e.g. administered to a subject)

to interfere with the interaction of gp39 on a T cell with a gp39 ligand on an antigen presenting cell, such as a B cell. A gp39 antagonist is defined as a molecule which interferes with this interaction. The gp39 antagonist can be an antibody directed against gp39 (e.g., a monoclonal antibody against gp39), a fragment or derivative of an antibody directed against gp39 (e.g., Fab or F(ab)'2 fragments, chimeric antibodies or humanized antibodies), soluble forms of a gp39 ligand (e.g., soluble CD40), soluble forms of a fusion protein of a gp39 ligand (e.g., soluble CD40Ig), or pharmaceutical agents which disrupt or interfere with the gp39-CD40 interaction.

A. Antibodies

A mammal, (e.g., a mouse, hamster, or rabbit) can be immunized with an immunogenic form of gp39 protein or protein fragment (e.g., peptide fragment) which elicits an antibody response in the mammal. A cell which expresses gp39 on its surface can also be used as the immunogen. Alternative immunogens include purified gp39 protein or protein fragments. gp39 can be purified from a gp39-expressing cell by standard purification techniques; gp39 cDNA (Armitage et al., *Nature*, 357:80–82 (1992); Lederman et al., *J. Exp. Med.*, 175:1091–1101 (1992); Hollenbaugh et al., *EMBO J.*, 11:4313–4319 (1992)) can be expressed in a host cell, e.g., bacteria or a mammalian cell line, and gp39 protein purified from the cell culture by standard techniques. gp39 peptides can be synthesized based upon the amino acid sequence of gp39 (disclosed in Armitage et al., *Nature*, 357:80–82 (1992); Lederman et al., *J. Exp. Med.*, 175:1091–1101 (1992); Hollenbaugh et al., *EMBO J.*, 11:4313–4319 (1992)) using known techniques (e.g. F-moc or T-boc chemical synthesis). Techniques for conferring immunogenicity on a protein include conjugation to carriers or other techniques well known in the art. For example, the protein can be administered in the presence of adjuvant. The progress of immunization can be monitored by detection of antibody titers in plasma or serum. Standard ELISA or other immunoassay can be used with the immunogen as antigen to assess the levels of antibodies.

Following immunization, antisera can be obtained and, if desired, polyclonal antibodies isolated from the sera. To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art. For example, the hybridoma technique originally developed by Kohler and Milstein (*Nature* (1975) 256:495–497) as well as other techniques such as the human B-cell hybridoma technique (Kozbar et al., *Immunol Today* (1983) 4:72), the EBV-hybridoma technique to produce human monoclonal antibodies (Cole et al. *Monoclonal Antibodies in Cancer Therapy* (1985) (Allen R. Bliss, Inc., pages 77–96), and screening of combinatorial antibody libraries (Huse et al., *Science* (1989) 246:1275). Hybridoma cells can be screened immunochemically for production of antibodies specifically reactive with the protein or peptide and monoclonal antibodies isolated.

The term antibody as used herein is intended to include fragments thereof which are specifically reactive with a gp39 protein or peptide thereof or gp39 fusion protein. Antibodies can be fragmented using conventional techniques and the fragments screened for utility in the same manner as described above for whole antibodies. For example, F(ab')₂ fragments can be generated by treating antibody with pepsin. The resulting F(ab')₂ fragment can be treated to reduce disulfide bridges to produce Fab' fragments. The antibody of the present invention is further intended to include bispecific and chimeric molecules having an anti-gp39 portion.

When antibodies produced in non-human subjects are used therapeutically in humans, they are recognized to varying degrees as foreign and an immune response may be generated in the patient. One approach for minimizing or eliminating this problem, which is preferable to general immunosuppression, is to produce chimeric antibody derivatives, i.e., antibody molecules that combine a non-human animal variable region and a human constant region. Chimeric antibody molecules can include, for example, the antigen binding domain from an antibody of a mouse, rat, or other species, with human constant regions. A variety of approaches for making chimeric antibodies have been described and can be used to make chimeric antibodies containing the immunoglobulin variable region which recognizes gp39. See, for example, Morrison et al., *Proc. Natl. Acad. Sci. U.S.A.* 81:6851 (1985); Takeda et al., *Nature* 314:452 (1985), Cabilly et al., U.S. Pat. No. 4,816,567; Boss et al., U.S. Pat. No. 4,816,397; Tanaguchi et al., European Patent Publication EP171496; European Patent Publication 0173494, United Kingdom Patent GB 2177096B. It is expected that such chimeric antibodies would be less immunogenic in a human subject than the corresponding non-chimeric antibody.

For human therapeutic purposes the monoclonal or chimeric antibodies specifically reactive with a gp39 protein or peptide can be further humanized by producing human variable region chimeras, in which parts of the variable regions, especially the conserved framework regions of the antigen-binding domain, are of human origin and only the hypervariable regions are of non-human origin. Such altered immunoglobulin molecules may be made by any of several techniques known in the art, (e.g., Teng et al., *Proc. Natl. Acad. Sci. U.S.A.*, 80:7308–7312 (1983); Kozbor et al., *Immunology Today*, 4:7279 (1983); Olsson et al., *Meth. Enzymol.*, 92:3–16 (1982)), and are preferably made according to the teachings of PCT Publication WO92/06193 or EP 0239400. Humanized antibodies can be commercially produced by, for example, Scotgen Limited, 2 Holly Road, Twickenham, Middlesex, Great Britain.

Another method of generating specific antibodies, or antibody fragments, reactive against a gp39 protein or peptide is to screen expression libraries encoding immunoglobulin genes, or portions thereof, expressed in bacteria with a gp39 protein or peptide. For example, complete Fab fragments, VH regions and FV regions can be expressed in bacteria using phage expression libraries. See for example Ward et al., *Nature*, 341: 544–546: (1989); Huse et al., *Science*, 246: 1275–1281 (1989); and McCafferty et al., *Nature*, 348: 552–554 (1990). Screening such libraries with, for example, a gp39 peptide can identify imunoglobin fragments reactive with gp39. Alternatively, the SCID-hu mouse (available from Genpharm) can be used to produce antibodies, or fragments thereof.

Methodologies for producing monoclonal antibodies directed against gp39, including human gp39 and mouse gp39, and suitable monoclonal antibodies for use in the methods of the invention, are described in further detail in Example 6. Particularly preferred anti-human gp39 antibodies of the invention are mAbs 24-31 and 89-76, produced respectively by hybridomas 24-31 and 89-76. The 89-76 and 24-31 hybridomas, producing the 89-76 and 24-31 antibodies, respectively, were deposited under the provisions of the Budapest Treaty with the American Type Culture Collection, Parklawn Drive, Rockville, Md., on Sep.

2, 1994. The 89-76 hybridoma was assigned ATCC Accession Number HB11712 and the 24-31 hybridoma was assigned ATCC Accession Number HB11713.

Recombinant anti-gp39 antibodies, such as chimeric and humanized antibodies, can be produced by manipulating nucleic acid (e.g., DNA) encoding an anti-gp39 antibody according to standard recombinant DNA techniques. Accordingly, another aspect of this invention pertains to isolated nucleic acid molecules encoding immunoglobulin heavy or light chains, or portions thereof, reactive with gp39, particularly human gp39. The immunoglobulin-encoding nucleic acid can encode an immunoglobulin light or heavy chain variable region, with or without a linked heavy or light chain constant region (or portion thereof). Such nucleic acid can be isolated from a cell (e.g., hybridoma) producing an anti-human gp39 mAb by standard techniques. For example, nucleic acid encoding the 24-31 or 89-76 mAb can be isolated from the 24-31 or 89-76 hybridoma, respectively, by cDNA library screening, PCR amplification or other standard technique. Following isolation of, and possible further manipulation of. Moreover, nucleic acid encoding an anti-human gp39 mAb can be incorporated into an expression vector and introduced into a host cell to facilitate expression and production of recombinant forms of anti-human gp39 antibodies.

B. Soluble Ligands for gp39

Other gp39 antagonists which can be used to induce T cell tolerance are soluble forms of a gp39 ligand. A monovalent soluble ligand of gp39, such as soluble CD40 can bind gp39, thereby inhibiting the interaction of gp39 with CD40 on B cells. The term "soluble" indicates that the ligand is not permanently associated with a cell membrane. A soluble gp39 ligand can be prepared by chemical synthesis, or, preferably by recombinant DNA techniques, for example by expressing only the extracellular domain (absent the transmembrane and cytoplasmic domains) of the ligand. A preferred soluble gp39 ligand is soluble CD40. Alternatively, a soluble gp39 ligand can be in the form of a fusion protein. Such a fusion protein comprises at least a portion of the gp39 ligand attached to a second molecule. For example, CD40 can be expressed as a fusion protein with immunoglobulin (i.e., a CD40Ig fusion protein). In one embodiment, a fusion protein is produced comprising amino acid residues of an extracellular domain portion of the CD40 molecule joined to amino acid residues of a sequence corresponding to the hinge, CH2 and CH3 regions of an immunoglobulin heavy chain, e.g., Cγ1, to form a CD40Ig fusion protein (see e.g., Linsley et al. (1991) *J. Exp. Med.* 1783:721–730; Capon et al. (1989) *Nature* 337, 525–531; and Capon U.S. Pat. No. 5,116,964). The fusion protein can be produced by chemical synthesis, or, preferably by recombinant DNA techniques based on the cDNA of CD40 (Stamenkovic et al., *EMBO J.*, 8:1403–1410 (1989)).

II. Cells for Induction of Antigen-Specific Tolerance

The current invention is based, at least in part, on the discovery that presentation of an antigen to a T cell by a cell which both presents antigen and interacts with gp39 results in antigen-specific T cell tolerance when the antigen is presented to the T cell in the presence of a gp39 antagonist. Cells which are capable of inducing T cell tolerance by this mechanism include those which present antigen to a T cell and require an interaction between a gp39 ligand on the cell and gp39 on the T cell to deliver the necessary signals for T cell activation to the T cell. Inhibition of this interaction prevents T cell activation by the presented antigen and, rather, induces antigen-specific tolerance in the T cell. Interference with activation of the T cell via gp39 may prevent the induction of costimulatory molecules on the antigen presenting cell (e.g., B7 family molecules on an antigen presenting cell such as a B cell) so that the antigen presenting cell delivers only an antigenic signal in the absence of a costimulatory signal, thus inducing tolerance.

Accordingly, in the methods of the invention, a cell which presents antigen is administered to a recipient subject. The phrase "cell which presents antigen" and "antigen presenting cell" are used interchangeably herein and are intended to encompass cells which can present antigen to T cells of the recipient and includes B lymphocytes, "professional" antigen presenting cells (e.g., monocytes, dendritic cells, Langerhan cells) and other cells which present antigen to immune cells (e.g., keratinocytes, endothelial cells, astrocytes, fibroblasts, oligodendrocytes). Furthermore, it is preferable that the antigen presenting cell have a reduced capacity to stimulate a costimulatory signal in recipient T cells. For example, the antigen presenting cell may lack expression of or express only low levels of costimulatory molecules such as the B7 family of proteins (e.g., B7-1 and B7-2). Expression of costimulatory molecules on potential antigen presenting cells to be used in the method of the invention can be assessed by standard techniques, for example by flow cytometry using antibodies directed against costimulatory molecules.

Preferred antigen presenting cells for inducing T cell tolerance are lymphoid cells, for example peripheral blood lymphocytes or splenic cells. Preferred lymphoid cells for inducing T cell tolerance are B cells. B cells can be purified from a mixed population of cells (e.g., other cell types in peripheral blood or spleen) by standard cell separation techniques. For example, adherent cells can be removed by culturing spleen cells on plastic dishes and recovering the non-adherent cell population. T cells can be removed from a mixed population of cells by treatment with an anti-T cell antibody (e.g., anti-Thy1.1 and/or anti-Thy1.2) and complement. In one embodiment, resting lymphoid cells, preferably resting B cells, are used as the antigen presenting cells. Resting lymphoid cells, such as resting B cells, can be isolated by techniques known in the art, for example based upon their small size and density. Resting lymphoid cells can be isolated for example by counterflow centrifugal elutriation as described in Tony, H -P. and Parker, D. C. (1985) *J. Exp. Med.* 161:223–241. Using counterflow centrifugal elutriation, a small, resting lymphoid cell population depleted of cells which can activate T cell responses can be obtained by collecting a fraction(s) at 14–19 ml/min., preferably 19 ml/min. (at 3,200 rpm). Alternatively, small, resting lymphocytes (e.g., B cells) can be isolated by discontinuous density gradient centrifugation, for example using a Ficoll or Percoll gradient, and a layer containing small, resting lymphocytes can be obtained after centrifugation. Small resting B cells can also be distinguished from activated B cells by assaying for expression of costimulatory molecules, such as B7-1 and/or B7-2, on the surface of activated B cells by standard techniques (e.g., immunofluorescence).

The antigen presenting cell, such as a B cell, can be contacted with an antigen (e.g., a soluble protein) prior to contact with the T cell (e.g., prior to administration to a subject) and the cell used to present the antigen to the T cell in the presence of a gp39 antagonist to induce specific T cell tolerance to the antigen (see Example 1). Alternatively, tolerance to alloantigens can be induced by using an allogeneic cell as the antigen presenting cell (see Examples 2 and 3). The allogeneic cell presents antigenic fragments of allogeneic proteins to T cells. In one embodiment, the allogeneic cell is an allogeneic lymphoid cell, such as an allogeneic B cell. Alternatively, a subject can be tolerized with cells in peripheral blood (e.g., peripheral blood lymphocytes), splenic cells or bone marrow cells. In the case of bone marrow transplantation, the donor bone marrow cells themselves serve as the antigen presenting cells contacted with the T cells (e.g., administered to a subject). Accordingly, allogeneic bone marrow can be administered in conjunction with a gp39 antagonist to induce tolerance to the bone marrow in the recipient and to prevent graft versus host disease (see Examples 4 and 5).

III. Administration of Cells and gp39 Antagonists

Antigen-specific T cell tolerance can be induced according to the invention by administration of a gp39 antagonist to a subject in conjunction with a cell which presents antigen to a T cell and expresses a ligand which interacts with gp39 on the T cell. In a preferred embodiment, the antigen presenting cell and the gp39 antagonist are administered simultaneously or contemporaneously. Alternatively, the gp39 antagonist can be administered prior to administering the cells, for example when the antagonist is an antibody with a long half-life. In a case where the cells to be administered are bone marrow cells, wherein inhibition of graft-versus-host disease is desired, the donor T cells in the bone marrow can be tolerized before transfer to the recipient host by incubating the donor bone marrow with B cells from the host and a gp39 antagonist in vitro. gp39 treatment can be continued in vivo during and after bone marrow transfer if necessary. In subjects who are to receive a bone marrow or other organ transplant, allogeneic tolerance to the transplant can be induced in the subject by treatment with a regimen which induces allogeneic tolerance prior to transfer of the organ or bone marrow cells. This pretreatment regimen can involve administering to the subject cells from the donor together with a gp39 antagonist. The cells from the donor can be, for example, B cells, whole peripheral blood or some fraction thereof (e.g., peripheral blood lymphocytes or small resting lymphocytes or B cells).

Administration of a single dose of antigen presenting cells (in combination with the antagonist) has been found to be sufficient for induction of T cell tolerance (see the Examples). The number of antigen presenting cells administered may vary depending upon the type of cell used, the type of tissue or organ graft, the weight of the recipient, the general condition of the recipient and other variables known to the skilled artisan. An appropriate number of cells for use in the method of the invention can be determined by one of ordinary skill in the art by conventional methods (for example using assays described in the Examples). Cells are administered in a form and by a route which is suitable for induction of tolerance in the recipient. Cells can be administered in a physiologically acceptable solution, such as a buffered saline solution or similar vehicle. Cells are preferably administered intravenously.

An antagonist of the invention is administered to subjects in a biologically compatible form suitable for pharmaceutical administration in vivo to induce T cell tolerance. By "biologically compatible form suitable for administration in vivo" is meant a form of the antagonist to be administered in which any toxic effects are outweighed by the therapeutic effects of the protein. The term subject is intended to include living organisms in which an immune response can be elicited, e.g., mammals. Examples of subjects include humans, dogs, cats, mice, rats, and transgenic species thereof. A gp39 antagonist can be administered in any pharmacological form, optionally in a pharmaceutically acceptable carrier. Administration of a therapeutically active amount of the antagonist is defined as an amount effective, at dosages and for periods of time necessay to achieve the desired result. For example, a therapeutically active amount of an antagonist of gp39 may vary according to factors such as the disease state, age, sex, and weight of the individual, and the ability of the antagonist to elicit a desired response in the individual. Dosage regima may be adjusted to provide the optimum therapeutic response. For example, several divided doses may be administered daily or the dose may be proportionally reduced as indicated by the exigencies of the therapeutic situation.

The active compound (e.g., antagonist) may be administered in a convenient manner such as by injection (subcutaneous, intravenous, etc.), oral administration, inhalation, transdermal application, or rectal administration. Depending on the route of administration, the active compound may be coated in a material to protect the compound from the action of enzymes, acids and other natural conditions which may inactivate the compound. A preferred route of administration is by intravenous injection.

To administer an antagonist of gp39 by other than parenteral administration, it may be necessary to coat the antagonist with, or co-administer the antagonist with, a material to prevent its inactivation. For example, an antagonist can be administered to an individual in an appropriate carrier or diluent, co-administered with enzyme inhibitors or in an appropriate carrier such as liposomes. Pharmaceutically acceptable diluents include saline and aqueous buffer solutions. Enzyme inhibitors include pancreatic trypsin inhibitor, diisopropyl-fluorophosphate (DEP) and trasylol. Liposomes include water-in-oil-in-water emulsions as well as conventional liposomes (Strejan et al., (1984) *J. Neuroimmunol* 7:27).

The active compound may also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, asorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating active compound (e.g., an antagonist of gp39) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (e.g., antagonist) plus any additional desired ingredient from a previously sterile-filtered solution thereof.

When the active compound is suitably protected, as described above, the protein may be orally administered, for example, with an inert diluent or an assimilable edible carrier. As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

In addition to tolerization of T cell in vivo, the invention encompasses tolerization of T cells in vitro, e.g., by contact with an antigen presenting cell in the presence of a gp39 antagonist. For example, T cells can be obtained from a subject, tolerized in vitro by culture with the antigen presenting cells and the antagonist and then readministered to the subject.

IV. Uses of the Method of the Invention

The methods of the invention can be applied to induce T cell tolerance to a variety of antigens. For example, T cell tolerance can be induced to a soluble antigen (e.g., a soluble protein), as described in Example 1. T cells can be tolerized to antigens involved in autoimmune diseases or disorders associated with abnormal immune responses. For example, in one embodiment, the antigen is an autoantigen. In another embodiment, the antigen is an allergan. Alternatively, T cells can be tolerized to antigens expressed on foreign cells (as described in Examples 2 to 5). Accordingly, in yet other embodiments, the antigen is an alloantigen or xenoantigen. Induction of T cell tolerance to alloantigens and xenoantigens is of particular use in transplantation, for example to inhibit rejection by a transplant recipient of a donor graft, e.g. a tissue or organ graft or bone marrow transplant. Additionally, tolerization of donor T cells within a bone marrow graft is useful for inhibiting graft versus host disease (see Example 5).

The invention is further illustrated by the following exampes which should not be construed as limiting. The contents of all references, patents and published patent applications cited throughout this application are hereby incorporated by reference.

EXAMPLE 1

Induction of Antigen-Specific Tolerance
Methods

Mice were immunized with KLH-pulsed splenic B lymphocytes for 5 days. During the primary immunization animals were either untreated or treated with an anti-gp39 antibody MR1. Five days after the initial immunization, mice were given a local (food pad) challenge with KLH in complete Freund's adjuvant (CFA). Mice were sacrificed 5 days later, the draining lymph nodes removed and the T cell proliferative response to KLH was subsequently assayed in vitro.

Results

Figure 1:
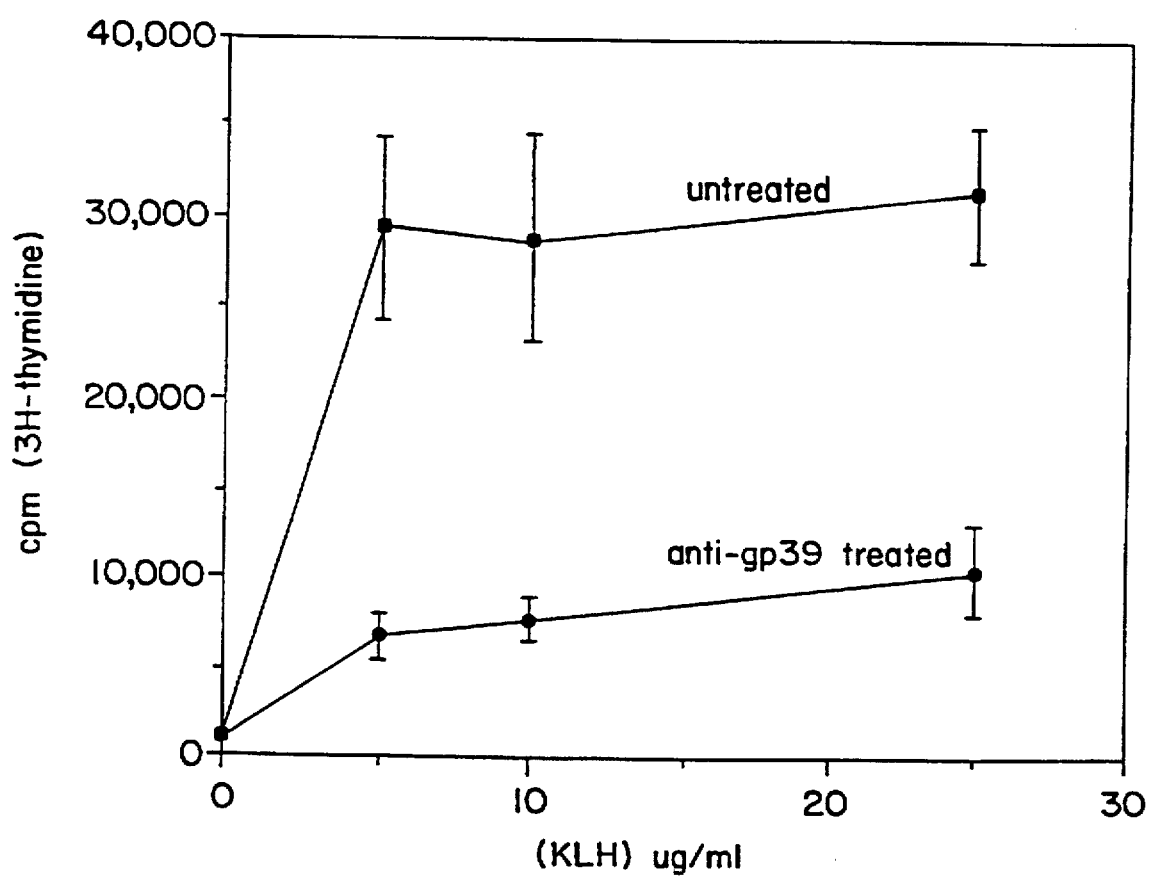
FIG. 1 is a graphic representation of T cell tolerance to a protein antigen induced by in vivo anti-gp39 treatment. T cells responses were measured in vitro upon challenge with an antigen which previously was administered in vivo on antigen-pulsed B cells either with or without an anti-gp39 antibody.

Animals immunized with activated B lymphocytes pulsed with antigen and subsequently challenged with the same antigen mount significant immune responses to the immunizing antigen. The response measured by proliferation of antigen-specific T lymphocytes is shown in FIG. 1. Treatment of animals with an anti-gp39 antibody during the primary immunization results in unresponsiveness of antigen-specific T lymphocytes upon in vitro antigen challenge. T lymphocytes obtained from lymph nodes from animals treated with an anti-gp39 antibody show decreased proliferative capacity when compared to T lymphocytes obtained from lymph nodes of untreated animals.

EXAMPLE 2

Induction of T Cell Tolerance to Allogeneic Cells
Methods

Balb/c ($H-2^d$) mice were immunized with allogeneic splenic B cells from DBA/2 ($H-2^b$) mice. Animals were treated with an anti-gp39 antibody, MR1, or untreated for 5 days after immunization. On day 6, the animals were sacrificed and spleens removed. Spleen cells from anti-gp39 antibody or untreated animals were subsequently cultured in vitro with either no stimulus or with irradiated DBA/2 spleen cells. The proliferative response to this secondary allogeneic stimulation was measured on day 3 after initiation of culture.

Results

Figure 2:
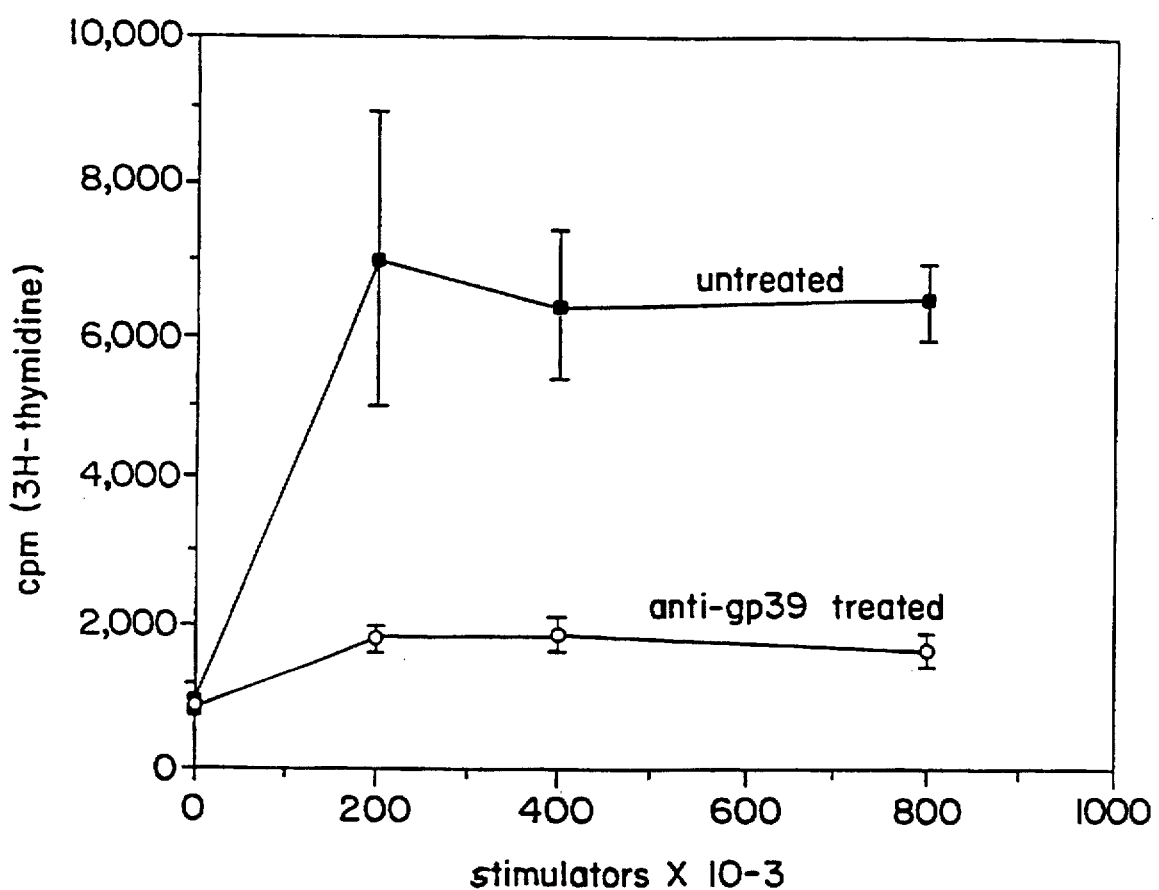
FIG. 2 is a graphic representation of T cell tolerance to allogeneic B cells induced by in vivo anti-gp39 treatment. T cells responses were measured in vitro upon challenge with allogeneic B cells which previously were administered in vivo either with or without an anti-gp39 antibody.

T lymphocytes from animals immunized with allogeneic splenic B cells mount strong proliferative responses when challenged 5 days later with the same cells in vitro (FIG. 2). However, T lymphocytes from mice immunized with allogeneic splenic B cells and treated with an anti-gp39 antibody have a decreased proliferative capacity when subsequently challenged ion vitro. Anti-gp39 antibody treated mice exhibit approximately 50% decrease in responsiveness to challenge compared to control untreated mice.

EXAMPLE 3

Anti-gp39 Treatment Interferes with the Generation of CTL Responses to Allogeneic B Cells In this example, the role of gp39 in the generation of cytotoxic T cells (CTL) was investigated. To assess the in vivo function of gp39 in the development of CTL, the effects of anti-gp39 treatment on the generation of allospecific CTL by immunization with allogeneic B cells was examined. Effects of anti-gp39 treatment of both primary and secondary CTL responses were determined.

Primary CTL Responses

To test whether anti-gp39 can prevent allogeneic B cells from eliciting allospecific CTL responses in vivo, allogeneic B cells (T-depleted spleen cells) were administered to recipient mice with or without anti-gp39. Balb/c mice (female, 6–8 weeks old, Jackson Laboratories, Bar Harbor, Me.) were immunized with C57BL/6 (female, 6–8 weeks old, Jackson Laboratories, Bar Harbor, Me.) spleen cells (30–50×10$^6$) depleted of T cells by anti-Thy1.2 (ascites prepared from ATCC clone HO13.4) and rabbit complement treatment. These recipient mice were then untreated or treated with anti-gp39 for 5 days (250 mg/recipient on days 0, 2 and 4). On day five, spleens were removed and CTL responses were measured using a 4 hour chromium release assay. Spleen cells from unprimed Balb/c mice were used as negative control effector cells. Target cells used were E female K1 (H-2$^b$, T cell lymphoma derived from C57BL/6 strain) and P815 (H-2$^d$, mastocytoma, derived from DBA/2J strain). $^{51}$Cr-labelled target cells were washed and plated at 1×10$^4$ cells per well in 96 well plates with effector cells in effector:target (E:T) ratios of 100:1, 20:1 and 4:1. The plates were briefly centrifuged and then incubated at 37° C. in 5% CO$_2$ for 4 hours. The plates were once more centrifuged and 100 ml of cell-free supernatant was collected from each well for gamma counting (LKB Clinigamma, Wallace Inc., Gaithersburg, Md.). Percent specific lysis is defined as (a-b)/c, where a=cpm released by target cells incubated with effector cells, b=cpm released by target cells incubated with media only (spontaneous release) and c=freeze-thaw releasable cpm from target cells (approximately 80% of total cpm incorporated). P815 targets were not lysed by any of the cell samples tested. Results for E female K1 targets are illustrated in FIG. 3A, wherein the groups shown are untreated mice (■), anti-gp39 treated mice (△) and spleen cells from unprimed Balb/c mice (●; used as negative control effector cells). The results demonstrate that mice that received anti-gp39 and allogeneic cells did not generate a primary CTL response in vivo in response to allogeneic B cells. In contrast, in the absence of anti-gp39, the allogeneic B cells sensitized the recipient to alloantigen and induced a substantial CTL response.

To determine if anti-gp39 could only amplify the tolerogenic effect of non-activated, splenic B cells, LPS-activated B cells were used to prime CTL in the presence or absence of anti-gp39. B cells from C57BL/6 mice were prepared as described above and cultured for 2 days in the presence or absence of lipopolysaccharide (LPS; 50 mg/ml; Sigma Diagnostics, St. Louis, Mo.). Cells were then harvested and washed thoroughly and injected i.p. (30–50×10$^6$) into Balb/c recipient mice. Recipient mice were either untreated or treated with anti-gp39 on days 0, 2 and 4 as described above. On day 5, spleens were removed and CTL responses were determined as described above. The results of two independent experiments are shown in FIG. 3B (top and bottom panels). Groups represented are LPS blasts in vivo without treatment (>), LPS blasts in vivo with anti-gp39 treatment (●), resting B cells in vivo without treatment (○) and resting B cells in vivo with anti-gp39 treatment (□). The results indicate that, although not complete, anti-gp39 treatment also reduced the primary CTL response to allogeneic LPS blasts.

Secondary CTL Responses

To examine the impact of anti-gp39 and allogeneic B cell administration on CTL formation, spleen cells from treated and untreated mice were stimulated in vitro and the scope of CTL responses investigated. Balb/c mice were primed in vivo with C57BL/6-derived B cells as described above. Spleen cells from the anti-gp39 and control hamster Ig (HIg)-treated animals were removed and 5×10$^6$ cells/ml were cultured for 5 days ("responders") with various mitomycin C treated (2.5 mg/ml at 37° C., Sigma Diagnostics, St. Louis, Mo.) strains of splenic B cells (prepared by anti-Thy1.2+complement treatment) at 5×10$^6$ stimulators/ml. Stimulator groups were C57BL/6 (H-2$^b$) and Balb/c (H-2$^d$) which indicate the secondary allogeneic response and the primary syngeneic response, respectively. Stimulator and responder cells were cultured in freshly prepared sensitization RPMI-1640 medium (Bio Whittaker, Walkersville, Md.), 1×10$^5$M 2-mercaptoethanol (Bio-Rad Laboratories, Hercules, Calif.), 2 mM L-glutamine (Sigma Diagnostics, St. Louis, Mo.), 500 U/ml penecillin and 5000 U/ml streptomycin (Sigma Diagnostics, St. Louis, Mo.). After 5 days, the responder cells were harvested and dead cells were removed by centrifugation on a density gradient. The resulting live cells were used as effectors in a CTL assay as described above. Targets included E female K1 (H-2$^b$, T cell lymphoma derived from C57BL/6 strain) and P815 (H-2$^d$, mastocytoma, derived from DBA/2J strain). The results are illustrated in FIG. 4A. Allogeneic stimulated effector groups shown are: HIg treated recipients (●), naive Balb/c (>) and anti-gp39 treated recipients (■). Corresponding syngeneic response (Balb/c cells stimulated with Balb/c cells) are indicated by open symbols. As anticipated, in vivo immunization of mice with allogeneic T-depleted spleen cells (H-2$^b$) in the absence of anti-gp39 treatment resulted in a robust secondary CTL response in vitro. The heightened secondary anti-H-2$^b$ CTL response was not observed if mice were given anti-gp39 in vivo.

To determine the specificity of the inhibition of CTL responses by anti-gp39 treatment, spleen cell cultures as described above were analyzed for anti-H-2$^k$ allogeneic responses (third party allogeneic responses) using B10BR (H-2$^k$) splenic B cells as the stimulators and SL8 (H-2$^k$, spontaneous T cell lymphoma derived from AKR strain) as the targets in the CTL assay. The results are shown in FIG. 4B. Groups shown are naive Balb/c (○) and anti-gp39 treated recipients (■). The results demonstrate that the inhibition of anti-H2$^b$-specific CTL responses by anti-gp39 treatement was allospecific since administration of H-2$^b$ spleen cells and anti-gp39 did not alter the in vitro CTL response to a bystander alloantigen (H-2$^k$).

Taken together, these data show that anti-gp39 interferes with the generation of allospecific CTL responses (both primary and secondary). In the presence of anti-gp39, CTL precursors specific to the relevant alloantigen are still present since in the in vitro secondary culture one can demonstrate some anti-H-2$^b$ CTL activity. It can be concluded that anti-gp39 treatment reduced the secondary in vitro response by blocking CTL priming or reducing the frequency of primed allospecific CTL. The use of resting B cells is not imperative to demonstrate this unresponsiveness since the allogeneic CTL response induced by LPS blasts was also impaired by anti-gp39.

EXAMPLE 4

Transfer of Allogeneic Murine Bone Marrow Induces Stable Chimeras when Recipients are Treated with an Antibody to gp39

The treatment for many hematological disorders, that cannot be cured with conventional chemotherapeutic methods, involves the transfer of allogeneic bone marrow. This aggressive therapy involves administration of high, myeloablative doses of chemotherapy coupled with the perfusion of allogeneic bone marrow allowing the eradication of clonogenic tumor cells.

It has already been shown that thymic irradiation, deleting thymic T cells, increases the incidence of stable chimeras when monoclonal antibodies (mAbs) to T cell, including anti-CD4 mAbs were used. This antibody regime led to T cell deletion and thus donor specific tolerance, which could be indicated by tolerance to donor skin grafts. Failure to achieve permanent allogeneic engraftment after 300 rad WBI, in vivo anti-T cell mAb treatment, and administration of allogeneic bone marrow may have resulted from the unaffected T cells within the thymus. Use of anti-CD4 and anti-CD8 mAbs can lead to effective depletion of peripheral blood and splenic T cells, but the thymic T cells are simply coated with mAbs but not deleted. Thus thymic irradiation is performed on the mice.

Methods

A murine model for allogeneic bone marrow transfer (BMT) of F1 into parent was used so as to avoid graft-versus-host disease from being induced. We used the F1 strain CB6 which are (C57BL/6×Balb/c)F1 resulting the overall MHC haplotype of $H-2^{d/b}$. Bone marrow was removed and i.v. injected into the irradiated BALB/c parent with or without an anti-gp39 antibody, MR1. Whole body irradiation (WBI) levels were varied so as to determine the best level of chimerism and to compare anti-gp39 antibody treated and untreated animals with each irradiation level. Chimerism was determined by flow cytometric analysis of peripheral blood lymphocytes of the $H-2^b$ MHC haplotype present within the $H-2^d$ (BALB/c) mouse. It has previously been shown that this combination of mice is suitable and chimeras can be obtained at levels of 500 and 600 rads WBI.

Results

Chimerism was detected by identification of C57BL/6 derived cells ($H-2^b$) by flow cytometry. Chimerism was found to develop in mice irradiated with 400, 500 and 600 whole body irradiation within 14 days only if treated with anti-gp39 antibody from the start of the study. Mice that received no antibody treatment rejected the cells at all levels of irradiation except when given 600 whole body irradiation, whereby they accepted the bone marrow to the same extent as the antibody treated group at 400 rads (Table 1). It was found that the level of chimerism after 6 weeks of therapy at 400, 500 and 600 rads with anti-gp39 antibody therapy to be 70.7+5.74, 94.1 and 84.4+8.56 respectively, while at 600 rads with no treatment they it was found to be 85.7+5.9 chimeric (Table 2). Phenotyping the cells at this point indicated that T cells, B cells and macrophages were all chimerised and the the same extent for 400 rads when treated compared to the 600 rads untreated group (Table 2). It also appeared that anti-gp39 antibody treatment did not significantly change the total percent population of any of the lymphoid cells within the periphery. When treatment of the animals with anti-gp39 antibody was terminated the animals were found to be stably chimeric for up to 8 weeks post transplant.

TABLE I

| Whole body radiation level (rads) | No. of chimeric animals treated with anti-gp39 treatment | No. of chimeric animals with no anti-gp39 treatment |
| --- | --- | --- |
| 0 | 0(5) | 0(5) |
| 200 | 0(5) | 0(5) |
| 400 | 9(9) | 0(9) |
| 450 | 3(5) | 0(5) |

TABLE I-continued

| Whole body radiation level (rads) | No. of chimeric animals treated with anti-gp39 treatment | No. of chimeric animals with no anti-gp39 treatment |
| --- | --- | --- |
| 500 | 4(5) | 2(5) |
| 600 | 7(9) | 7(9) |

Levels of whole body irradiation resulting in chimerism. Numbers in parenthesis indicate the total number of animal tested at each level.

TABLE 2

| Rads. | Treatment | $H-2K^{b+}$ | B cells $H-2K^{b+}$ | T cells $H-2K^{b+}$ | Mac. $H-2K^{b+}$ |
| --- | --- | --- | --- | --- | --- |
| 400 | + | 70.7 ± 5.74 | 89 ± 2.6 | 45.9 ± 13.3 | 82.3 ± 3.3 |
| 500 | + | 94.1 | 100 | 89 | 100 |
| 600 | + | 84.4 ± 8.56 | 99.3 ± 0.94 | 72.3 ± 15.9 | 91.1 ± 8.3 |
| 600 | − | 85.7 ± 5.9 | 97.3 ± 1.77 | 67.1 ± 10.3 | 91 ± 9 |

Percent of B cell, T cell and macrophages (Mac.) positive for $H-2Kb$ ± standard error.

EXAMPLE 5

Allogeneic Bone Marrow Transplantation Combined with Treatment of the Recipient with Anti-gp39 Inhibits Acute and Chronic Graft Versus Host Disease The following methodology was used in this example:

Mice: DBA/2 ($H-2^d$), C57BL/6 ($H-2^b$) and $B6D2F_1$ ((C57BL/6 ($H-2^d$)×DBA/2) $F_1$ hybrid) mice were obtained from the NCI laboratories (Bethesda, Md.) and maintained in a viral free environment in the Animal facility at Dartmouth Medical School. All the mice used in this study were female, and aged 6 to 8 weeks old.

Induction of chronic GVHD: Chronic GVHD was induced by the i.v. injection of parental (DBA/2) spleen cells into non-irradiated (C57BL/6×DBA/2) $F_1$ hybrid recipients (Fast, L. D. (1990) J. Immunol. 144:4177). Parental mice were anesthetized and killed by cervical dislocation in preparation for removal of the spleen. Dissociated spleen cells were washed and resuspended in RPMI 1640 medium (Whittaker, Waldersville, Md.) for i.v. injection into the $F_1$ recipients.

Induction of acute GVHD: Acute GVHD was induced by the i.v. injection of parental C57BL/6 spleen cells into non-irradiated (C57BL/6×DBA/2) $F_1$ hybrid recipients. Cells were prepared for transfer as for the induction of chronic GVHD.

Antibodies: Anti-gp39:MR1 was produced in ascites and purified by ion exchange HPLC, as previously described (Foy, T. M. et al. (1993) J. Exp. Med. 178:1567–1575; Noelle, R. J. et al. (1992) Proc. Natl. Acad. Sci. USA 89:6550). Polyclonal anti-isotype antibodies: All anti-$IgG_1$ and IgA antibodies and standard controls were obtained from Southern Biotechnology Associates, Inc., (Birmingham Ala.). Anti-IgE antibodies: All anti-IgE antibodies (B1E3 and Biotin AM95) and standards (A3B1) used in the IgE specific ELIZA were a kind gift from Dr. T. Waldschmidt, IA. Anti-MHC halpotype antibodies: $H-2K^b$ FITC conjugated antibody and $H-2D^d$ Biotin conjugated antibody were obtained from PharMingen (San Diego, Calif.)

Cell lines: Cell lines used included P815 ($H-2^d$) and LB27.4 ($H-2^{bxd}$), which were obtained from the American Type Culture Collection. The cell line c1.18.5 (H-2b) was obtained as a kind gift from Dr. William R. Green.

Polyclonal Ig production in vitro: Spleens from control and cGVHD mice were removed and single cell suspensions prepared. Cells were treated with Tris-buffered ammonium chloride to remove erythrocytes and total white blood cell counts determined by visual hemocytometer counting. Cells were incubated ($5\times10^6$) in 1 ml of complete (c)RPMI-1640 medium (supplemented with 10% fetal serum (Hyclone, Logan Utah, 25 mM HEPES, 2 mM L-glutamine, 5000 U/ml penicillin and 5000 mg/ml streptomycin) for 3 days at 37° C., 5% $CO_2$. Culture supernatants were collected by pelleting the cells and Ig was quantified by an isotype-specific ELISA assay.

Isotype-specific and antigen-specific ELISAs: ELISA for the detection of $IgG_1$ and IgA: Goat anti-mouse $IgG_1$ or IgA (10 µg/ml; Southern Biotechnology Associates, Inc., Birmingham Ala.) in PBS was absorbed onto wells of a 96-well polyvinyl microtitre plate for 1 hour at 37° C. then overnight at 4° C. Plates were washed and blocked with PBS containing 1% FCS for 1 hour at 37° C. Plates were washed again and the appropriate dilutions of supernatants and standard controls ($IgG_1$ and IgA, Southern Biotechnology Associates, Inc., Birmingham Ala.) were added for 2 hours at 37° C. After this time, the plates were washed 3 times and alkaline-phosphatase conjugated goat anti-mouse $IgG_1$ or IgA. (1/500 dilutions) (Southern Biotechnology Associates, Inc., Birmingham Ala.) were added for 2 hours at 37° C. Plates were thoroughly washed and phosphatase substrate (1 mg/ml; Sigma Diagnostics, St. Louis, Mo.) added resulting in the appropriate colour change. Readings were determined by an ELISA reader (Dynatech Laboratories, Inc.) at an absorbance of 410 nm. Concentrations of Ig were determined by comparison to the appropriate isotype standard curve and expressed as the mean+standard error (n=3).

ELISA for the detection of IgE: Wells of 96-well polyvinyl microtitre plate were coated with an anti-mouse IgE capture antibody (B1E3 (2 mg/ml)) overnight at 4° C. and then blocked with PBS containing 1% FCS for 1 hour at 37° C. Plates were washed again and the appropriate dilutions of supernatants and standard controls (A3B 1 (IgE)) were added for 2 hours at 37° C. Plates were thoroughly washed and the EM95-Biotin (5 mg/ml) was added to each well and incubated for 2 hours at 37° C. After this time, alkaline-phosphatase conjugated to streptavadin was added (1/500 dilution) for a further 2 hours and then washed thoroughly before the addition of phosphatase substrate (1 mg/ml; Sigma Diagnostics, St. Louis, Mo.) resulting in the appropriate colour change. Readings were determined by an ELISA reader (Dynatech Laboratories, Inc.) at an absorbance of 410 nm. Concentrations of Ig were determined by comparison to standard curve and expressed as the mean+standard error (n=3).

ELISA for the detection of anti-DNA Ab: Calf thymus DNA (Sigma, St. Louis, Mo.) (5 µg/ml) was dissolved in coupling buffer containing 0.1M sodium carbonate/sodium bicarbonate (pH 9.8). This was boiled for 10 minutes and then incubated on ice for 3 minutes. The OD 260 of the DNA was then determined and the concentration adjusted to obtain the required 5 µg/ml DNA. 100 µl was then added to the wells of a 96 well polyvinyl microtitre plate and incubated overnight at 4° C. The plate was then washed 3 times and blocked for 1 hour at 37° C. with PBS containing 1% FCS and 0.02% sodium azide. The plate was again washed and serial dilutions of serum samples was then added (100 ml) and incubated for 2 hours at 37° C. The detection antibody, goat anti mouse $IgG_1$ alkaline phosphatase was then added each well and incubated once again for 2 hours at 37° C. Plates were thoroughly washed and phosphatase substrate (1 mg/ml; Sigma Diagnostics, St. Louis, Mo.) added resulting in the appropriate colour change. Readings were determined by an ELISA reader (Dynatech Laboratories, Inc.) at an absorbance of 410 nm. Antibody titres were compared to a positive sera samples and results expressed in arbitrary units.

Flow Cytometric Analysis for the detection of donor derived cells. Spleens were removed from normal $BDF_1$, cGVHD mice treated with and without anti-gp39 and a single cell suspension was prepared. The cells were layered onto Ficoll-Hypaque (4:1) and then contrifuged at 2000 rpm for 20 minutes at room temperature. The resulting lymphocyte layer was removed and washed once with BSS containing 5% FCS. $1\times10^6$ cells, per tube, were used for staining in a 50 µl final volume. 50 µl of rat serum was added to each tube to prevent non specific binding of antibodies. Cells were stained with the (a) control antibodies: Rat Ig FITC (1:100 final dilution) and PE-Streptavidin (1:500 final dilution) and (b) FITC H-$2K^b$ and Biotin H-$2D^d$ (both 1:100 final dilution). Cells were incubated for 20 minutes on ice and then washed twice to remove any unbound antibodies. Finally PE-Streptavidin (1:500 final dilution) was added to the appropriate tube to detect the biotin conjugated antibody for another 20 minutes on ice. Cells were again washed twice ready for analysis on a Becton Dickinson FACScan. After positive gating via forward and side scatter, 10,000 events were collected per sample for determination of percent cells positive for the relevant MHC haplotype.

Chromium release assay for assessment of CTL assay. $^{51}$Cr-labelled target cells are washed and plated at $1\times10^4$ per well in 96 well plates with effector cells in E:T ratios of 100:1, 20:1, and 4:1. Target cells used included P815 (H-$2^d$), LB27.4 (H-$2^{bxd}$) and c118.5 (H-$2^b$). The plates are briefly centrifuged and then incubated at 37° C. in 5% $CO_2$ for 4 hours. The plates were once more centrifuged and an aliquot of cell-free supernatant was collected from each well for counting by a gamma counter. Percent specific lysis is defined as (a−b)/c where a=cpm released by target cells incubated with effector cells, b=cpm released by target cells incubated with media only (spontaneous release), and c=freeze-thaw releasable cpm for target cells (approximately 80% of total cpm incorporated).

Secondary stimulation of acute GVHD spleen cells in vitro. Acute GVHD spleens were removed from anti-gp39 treated, HIg treated or untreated animals. Spleens were red cell depleted and then aliquoted at $1\times10^4$ per cell well. Irradiated stimulator cells (P815) were added to the appropriate wells. After 7 days CTL assays were performed against the appropriate targets as previously mentioned.

Results

GVHD in mice results in splenomegaly. In the mouse, one of the consequences of cGVHD is the enlargement of the spleen. It is primarily the host's own cells that infiltrate and enlarge the spleen, although this is in response to the presence of donor cells (Rolink, A. G. et al. (1983) J. Exp. Med. 158:546). FIG. 5 indicates that at 7–14 days after the initiation of cGVHD, spleens contains almost twice the number of leukocytes compared to mice without cGVHD. Treatment of mice at the onset of cGVHD with anti-gp39 (250 µg/mouse, days 0,2,4, and 6), reduce the number of leukocytes/spleen in cGVHD mice to values that were identical to mice without disease.

GVHD-induced hyperproduction of polyclonal Immunoglobulin. It has been reported that hyper production of Ig occurs in mice with cGVHD due to cognate interactions between donor T cells and B cells (Morris, S. E. et al. (1990) *J. Exp. Med.* 171:503). To determine whether anti-gp39 inhibits hyper Ig production, mice with cGVHD were administered anti-gp39. On day 7 or 14, spleens were removed from control and cGVHD mice and the B cells assayed for the spontaneous production of $IgG_1$ and IgA in vitro. Splenocytes from mice with cGVHD produced high levels of IgA and $IgG_1$ (FIGS. 6A and 6B) in vitro. However, splenocytes from mice with cGVHD and treated with anti-gp39 (days 0, 2, 4 and 6) produced levels of $IgG_1$ and IgA identical to mice without disease. The addition of anti-gp39 to cultures of spleen cells from mice with cGVHD did not reduce the levels of in vitro Ig production, suggesting that anti-gp39 was exerting its effects in vivo.

When Hamster Ig (HIg) was used as a control for these experiments it was found that it showed no inhibitory role in the induction of GVHD but actually accentuated the disease not only in terms of polyclonal Ig production but also in the resultant spenomegaly. An 8-fold increase was detected in the level of Ig produced by 1 week HIg treated GVHD-induced mice compared to untreated 1 week GVHD-induced mice. It was apparent that the HIg was in itself an immunogen. Consequently it was decided to designate the untreated $F_1$ recipient mice as the relevant control group.

Effect of anti-gp39 on GVHD-induced serum Hyper-IgE and anti-DNA autoantibodies. The course of cGVHD can be monitored by the elevation in serum IgE and antibodies to double stranded DNA (Morris, S. E. et al. (1990) *J. Exp. Med.* 171:503). Levels of serum IgE were measured using an IgE specific ELISA. Chronic GVHD induced mice were treated with anti-gp39 on days 0, 2, 4 and 6 and then no further antibody was administered. Mice were bled at weekly intervals and the levels of serum IgE ascertained (FIG. 7A). cGVHD induces a 10–15 fold increase in serum IgE levels. Administration of anti-gp39 inhibited cGVHD-induced increases in serum IgE for up to eight weeks after the initiation of disease. In addition to the inhibition of elevated serum IgE, administration of anti-gp39 also blocked the generation of serum anti-DNA autoantibodies. Chronic GVHD induces a 5–10 fold increase in the levels of anti-DNA antibodies found, which was reduced by anti-gp39 treatment (FIG. 7B).

Previous studies have shown that the half-life of anti-gp39 (MR1 clone) is 12 days (Foy, T. M. et al. (1993) *J. Exp. Med.* 178:1567–1575). ELISA assays specific for the detection of anti-gp39 indicate that the anti-gp39 was undetectable in the serum of treated mice eight weeks following therapy. Therefore, persistent anti-gp39 cannot account for the protracted suppression of cGVHD. Transfer studies were performed to investigate if splenocytes from mice with cGVHD and those that have been administered anti-gp39 could transfer cGVHD. Splenocytes from mice given cGVHD and anti-gp39 were incapable of inducing heightened serum levels of IgE and anti-DNA autoantibodies upon adoptive transfer; whereas splenocytes from mice with cGHVD induced enhanced sIgE and anti-DNA antibodies. These data suggest that the alloreactive T cells have been induced to become unresponsive as a result of anti-gp39 treatment.

Detection of alloreactive donotrcells. When cGVHD induced mice were analysed for the presence of donor derived cells within their spleens, it was found that compared to normal $BDF_1$, which stain double positive for $H-2K^b$ and $H-2D^d$, cGVHD possessed approximately 5–7% donor cells. These cells are DBA/2 derived and therefore stain single positive for $H-2D^d$. These cells were detected irrespective of anti-gp39 treatment. This illustrate the point that anti-gp39 treatment allows engraftment of the donor cells without illiciting any of the helper function for the recipient B cells that results in polyclonal Ig production in the untreated cGVHD group.

Effect of anti-gp39 treatment on the induction of acute GVHD. Acute GVHD is associated with the induction of increased anti-allogeneic CTL response. While it is clear that gp39-CD40 interactions are critical for $T_h$-B cell interactions, it is not clear if the induction of other immune effector mechanisms may also be altered by anti-gp39 therapy. AGVHD was induced by the administration of C57BL/6 spleens to the $F_1$ recipients. As shown in FIG. 8, 12 days following the transfer of allogeneic cells, a robust $H-2^b$ anti $H-2^d$ CTL response is measured. Treatment of mice with anti-gp39, but not HIg, prevented the generation of $H-2^b$ anti-$H-2^d$ CTL (FIG. 8). In 1 of 2 experiments, treatment with anti-gp39 reduced the CTL responses below that which was observed with naive spleen cells. This suggested that spleen cells from a GVHD mice when challenged with. If these spleen cells are then cultured for 7 days in the presence of irradiated P815 cells and then a CTL assay performed these cells fail to mount a secondary stimulation to the P815 cells, however the normal $BDF_1$ spleen mount a primary response. The untreated aGVHD induced mice mount a secondary immune response as expected. These results indicate that the treatment of acute GVHD mice with anti-gp39 makes the CD8+ population unresponsive to a secondary challenge.

Discussion

Reversal of splenomegaly (FIG. 5), inhibition of hyper Ig production (FIGS. 6A and 6B), inhibition of serum levels of IgE and anti-DNA autoantibody production (FIGS. 7A and 7B) in GVH-induced mice by anti-gp39 administration, suggests that anti-gp39 blocked the ability of the grafted T cells to induce host B cell activation. This inhibition of spenomegaly and polyclonal $IgG_1$ and IgA production remains low 7 days after termination of antibody administration. Reduction in IgE and anti-DNA antibodies persists for 8 weeks even when the treatment is terminated. These results indicate that T cell function has been affected either by clonal deletion of the reactive T cells or that T cell anergy has occurred. It has previously been shown (Van den Eertwegh et al. (1993) *J. Exp. Med.* 178:1555–1565) that levels of cytokine producing cells remain normal in antibody treated mice in in situ studies of immunized mice. This indicates that T cells are not deleted as a consequence of the treatment. When cGVHD mice were analysed for the presence of donor derived cells they are found to be present whether the animal is untreated or treated with anti-gp39. Anti-gp39 thus has the ability to induce an unresponsive state upon these donor T cells, illiciting inhibition of antibody responses. Indeed, if spleens from these animals are transferred into naive recipients levels of antibody are elevated when the donor spleens are untreated cGVHD but anti-gp39 treated cGVHD mice are unable to mount a secondary cGVHD state upon transfer. This data suggests that anti-gp39 interferes with the ability of T cells to elicit a strong GVHD clinical immunopathology and splenomegaly that the antibody administration elicits unresponsiveness on the $CD4^+$ subpopulation.

It has been reported that B cells are required to provide help for the induction of CTLs as seen by studying B cell deficient mice for the induction of protective T cell immunity to a Friend murine leukemia virus-induced leukemia (Schultz, K. R. et al. (1990) *Science* 249). It thus seems conceivable that in a aGVHD induced mice, anti-gp39 inhibits the activation of B cells and thus prevents antigen presentation and thus prime the $CD8^+$ T cells. It has also been suggested that generation of CD8+ CTL required interaction with class II-restricted Th cells (von Boehmer, H. et al. (1979) *J. Exp. Med.* 150:1134; Keene, J. et al. (1982) *J. Exp. Med.* 155:768) and that when TCR affinity is low, CD4+ mediated T cell help is required in vivo (Gao, X. et al. (1991) *J. Immunol.* 147:3268).

Studies have been performed looking at the role of CD28-B7/BB1 interactions in the induction of CD8+CTL responses. It was found that CD28-B7/BB1 interactions were necessary and sufficient for the generation of class I MHC-specific CTL (Harding, F. A. and Allison, J. P. (1993) *J. Exp. Med.* 177:1791). It has been suggested that the ligand for CD40 may be an important inducer for B7 (Ranheim, E. A. and Kipps, T. J. (1993) *J. Exp. Med.* 177:925) as shown by studies involving the inhibition of B7 expression on normal and leukemic B cells by antibodies to CD40. Together, these studies indicate that anti-gp39 may block interaction of CD4+ T cells with B cells thus failing to induce the expression of B7 that allows a B cell to efficiently activate a T cell to proliferate and produce cytokines. Taken together, this data suggests that CD4+ T cells are required for the induction of CTL formation first by T-B cells cognate interaction between gp39 and its ligand CD40. Signaling of CD40 on the B cells then allows upregulation of B7/BB1. Reciprocal interaction of B7/BB1 with its ligand CD28 on the T cells then allows enhanced T cell proliferation and cytokine production. If, however, only one signal is provided to the T cells, i.e., gp39 interaction with CD40, and the second signal is not obtained, then an unresponsiveness is induced in the T cells and it becomes tolerised or anergised.

These studies indicate that when aGVHD is induced in mice, an anti-H-$2^d$ response is obtained. However, if the animals are treated with anti-gp39, then no CTL response is observed. It may be apparent that anti-gp39 is inhibiting the CTL formation by a method previously described (Schultz, K. R. et al. (1990) *Science* 249). The B cells fail to be activated via CD40 ligation and are thus unable to promote the induction of CTLs. Furthermore, our studies show that when spleen cells are challenged in vitro with P815 cells, the cells that were exposed to anti-gp39 in vivo were found unable to mount a secondary anti-H-$2^d$ CTL. Thus, this may indicate that anti-gp39 has induced a state of tolerance on the T cell compartment since gp39 is unable to engage CD40, there thus is no B7/BB1 upregulation and so the T cells do not get further activated and remain unresponsive. It is also known that resting B cells generally are ineffective stimulators of allogeneic T cells in the mixed lymphocyte reaction unless preactivated by anti-IgM antibodies, PMA or LPS (Inaba, K. and Steinman, R. M. (1989) *J. Exp. Med.* 160:1717; Metley, J. P. et al. (1989) *J. Exp. Med.* 169:239; Frohman, M. and Cowing, C. (1985) *J. Immunol.* 134:2269). In addition, soluble monomeric antigen directed to B cells for presentation in vivo may result in specific T cell anergy (Eynon, E. E. and Parker, D. (1992) *J. Exp. Med.* 175:131). Thus, it seems evident, depending on the method of administration of antigen and APCs involved, that anergy or tolerance may be induced. Upon challenge of P815 cells to the CD8+ T cells compartment of the spleen, B cells are not required for antigen presentation, thus alloantigen can be presented directly and CTL induced. The unresponsiveness of the spleens to secondary stimulation indicates that allospecific tolerance has been induced in this system.

This in opposition to previous results (Foy, T. M. et al. (1993) *J. Exp. Med.* 178:1567–1575) which indicate that tolerance is not induced by the antibody in an antigen specific system. The two systems differ since the aGVHD model presents alloantigen already bound to antigen presenting cells, whereas with antigen specific systems the antigen is administered and in vivo is taken up, processed and presented by professional APC. It thus seems that anti-gp39 may have different effects depending on the antigen being used and the method of presentation.

It can be concluded that anti-gp39 may induce allospecific tolerance in both the CD4+ and CD8+ compartments of the immune system and this may be obvious beneficial therapeutic intervention when considering transplant immunology and immunotherapy. It is conceivable that for treatment of patients undergoing bone marrow transplants that anti-gp39 therapy will be sufficient for induction of tolerance to the graft and prevent the induction of such consequences of transplant treatments as GVHD.

EXAMPLE 6

Production and Characterization of Anti-gp39 Antibodies

Experiment 1—Antibodies directed against human gp39

For induction of antigen-specific T cell tolerance in a human subject, it is preferable to administer an antibody directed against human gp39. The following methodology was used to produce mouse anti-human gp39 monoclonal antibodies. Balb/c mice were immunized with a soluble gp39 fusion protein, gp39-CD8, in Complete Freund's Adjuvant (CFA). Mice were subsequently challenged 6 weeks later with soluble gp39-CD8 in Incomplete Freund's Adjuvant (IFA). Soluble gp39-CD8 was given in soluble form 4 weeks after secondary immunization. Mice were then boosted with activated human peripheral blood lymphocytes 2 weeks later, followed by a final boost with soluble gp39-CD8 after an additional 2 weeks. Splenocytes were fused with the NS-1 fusion partner on day 4 after final immunization as per standard protocols.

Clones producing anti-human gp39 antibodies were selected based on a multiple screening process. Clones were initially screened by a plate binding assay using gp39-CD8. Positive clones were then screened against a control CD8 fusion protein, CD72-CD8. Clones which scored positive on the CD8-CD72 plate binding assay were eliminated. The remaining clones were subsequently screened on resting and 6 hour activated human peripheral blood lymphocytes (PBL) by flow cytometric analysis. Hybridomas staining activated, but not resting, PBL were considered positive. Finally, the remaining clones were tested for their ability to block the binding of CD40Ig to plate bound gp39.

Approximately 300 clones were initially screened against gp39-CD8 and CD72-CD8 in the plate binding assays. Of those clones, 30 were found to detect plate-bound gp39 and not CD8. These clones were subsequently screened for detection of gp39 on activated human PBL. Approximately 15 clones detected a molecule on activated PBL, but not resting cells. Specificity was further confirmed by determining the capacity of the clones to block CD40Ig detection of plate-bound gp39. 3 of 10 clones tested block CD40Ig binding in this assay. These clones were 3E4, 2H5 and 2H8. Such clones are preferred for use in the methods described herein. Clones which tested positive on activated, but not resting PBL, were also screened for reactivity with an activated rat T cell clone, POMC8. The clone 2H8 expressed crossreactivity with this rat T cell line.

Experiment 2—Antibodies directed against human gp39

A similar immunization procedure to that described in Experiment 1 was used to produce additional antibodies directed against human gp39. One BALB/c mouse was immunized with soluble gp39-CD8 in CFA, followed by challenge with 6 hour activated human peripheral blood lymphocytes 4 weeks later. The mouse was subsequently boosted with soluble gp39-CD8 4 days prior to fusion of splenocytes with the NS-1 fusion partner per standard protocols. Screening of hybridoma clones was performed by flow cytometric staining of 6 hour activated human PBLs. Clones staining activated but not resting human PBLs were selected. Six clones, 4D9-8, 4D9-9, 24-31, 24-43, 89-76 and 89-79, were selected for further analysis.

The specificity of the selected antibodies was confirmed by several assays. First, flow cytometric analysis demonstrated that all six mAbs stain activated, but not resting peripheral blood T cells (see FIG. 9B and 9C for a representative example, depicting staining of activated T cells with 4D9-8 and 4D9-9, respectively). Expression of the molecule recognized by each of the six antibodies is detectable within 4 hours of activation, is maximal between 6–8 hours after activation, and is undetectable by 24 hours after activation. All six mAbs recognize a molecule expressed on activated $CD3^+$ PBLs, predominantly of the CD4+ phenotype, but a portion of $CD8^+$ T cells also express the molecule. Expression of the molecule recognized by the six mAbs is inhibited by the presence of cyclosporin A in the culture medium, as is the expression of gp39 (see FIG. 10A and 10B for a representative example, depicting staining of cyclosporin treated T cells with 4D9-8 and 4D9-9, respectively). The kinetics and distribution of expression of the molecule recognized by these mAbs are identical to that of gp39, as detected by the fusion protein of human CD40Ig. In addition, all six mAbs block the staining of gp39 by CD40Ig (see FIG. 11A and 11B for for a representative example, depicting inhibition of gp39 staining by CD40Ig in the presence of 4D9-8 and 4D9-9, respectively). In an ELISA assay, all six mAbs recognize gp39-CD8, a soluble fusion form of the gp39 molecule. Moreover, all six mAbs immunoprecipitate a molecule of approximately 36 kd from $^{35}$S-methionine labeled activated human PBLs. The immunoprecipitated molecule is identical to that precipitated by the human CD40Ig fusion protein.

The functional activity of the six selected mAbs (4D9-8, 4D9-9, 24-32, 24-43, 89-76 and 89-79) was assayed as follows. First, the ability of the mAbs to inhibit the proliferation of purified human B cells cultured with IL-4 and soluble gp39 was measured. Purified human B cells were cultured with gp39 and IL-4 in the presence or absence of purified monoclonal antibodies or CD40Ig at dosages between 0 and 12.5 µg/ml. B cell proliferation was determined after 3 days in culture by thymidine incorporation. The results (shown in FIG. 12) demonstrate that all six mAbs can inhibit B cell proliferation induced by gp39 and IL-4. The mAbs 89-76 and 24-31 were most effective at inhibiting the induced B cell proliferation. The $IC_{50}$ (concentration of antibody necessary to inhibit B cell proliferation by 50%) was approximately 1 µg/ml for 89-76 and approximately 1.25 µg/ml for 24-31.

Next, the ability of the mAbs to inhibit B cell differentiation, as measured by Ig production induced by anti-CD3 activated T cells and IL-2, was examined. Purified $IgD^+$ human B cells were prepared by positive selection with FACS and then cultured with anti-CD3 activated human T cells (mitomycin C treated) and IL-2 for 6 days in the presence or absence of purified anti-gp39 monoclonal antibodies as dosages between 0 and 10 µg/ml. IgM, IgG and IgA production was assessed by ELISA on day 6. The results (shown below in Table 3) demonstrate that all six antibodies can inhibit T cell dependent B cell differentiation, as measured by IgM, IgG and IgA production. The $IC_{50}$ (concentration of antibody necessary to inhibit Ig production by 50%) was in the range of 1.0 µg/ml to below 0.1 µg/ml for the six mAbs, including the 24-31 and 89-76 antibodies.

TABLE 3

| mAb | µg/ml | Production of Immunoglobulin | | |
|---|---|---|---|---|
| | | IgM | IgG | IgA |
| none | — | 17,500 | 6710 | 4471 |
| 4D9-8 | 0.1 | 4813 | 2130 | 2819 |
| | 1.0 | 4394 | 2558 | 1519 |
| | 10.0 | 1081 | 389 | 396 |
| 4D9-9 | 0.1 | 3594 | 919 | 1731 |
| | 1.0 | 2659 | 1233 | 1606 |
| | 10.0 | 374 | 448 | 266 |
| 24-31 | 0.1 | 3863 | 981 | 344 |
| | 1.0 | 1287 | 314 | 165 |
| | 10.0 | 1120 | 596 | 23 |
| 24-43 | 0.1 | 6227 | 4132 | 432 |
| | 1.0 | 3193 | 2130 | 192 |
| | 10.0 | 7021 | 1232 | 1081 |
| 89-76 | 0.1 | 3783 | 1069 | 344 |
| | 1.0 | 2180 | 352 | 171 |
| | 10.0 | 818 | 551 | 19 |
| 89-79 | 0.1 | 9763 | 1924 | 3021 |
| | 1.0 | 2314 | 460 | 156 |
| | 10.0 | 183 | 135 | 434 |

To determine whether the six mAbs recognized distinct epitopes on the human gp39 molecule, crossblocking experiments were performed. Activated human PBLs were first blocked with each of the six mAbs (25 µg/ml of unconjugated antibody). Cells were washed and then stained with 10 µg/ml of biotin-conjugated antibody, followed by reaction with phytoerythrin conjugated avidin (PE-Av). The staining of the cells with PE-Av was analyzed by FACS. The results are shown below in Table 4.

TABLE 4

| Blocking Ab | Staining Antibody | | | | | |
|---|---|---|---|---|---|---|
| | 4D9-8 | 4D9-9 | 24-31 | 24-43 | 89-76 | 89-79 |
| none | +++ | +++ | ++++ | ++++ | ++++ | ++++ |
| 4D9-8 | ND | – | ++++ | ++++ | +++ | +++ |
| 4D9-9 | +++ | ND | +++ | ++++ | +++ | +++ |
| 24-31 | + | + | ND | +++ | ++ | ++ |
| 24-43 | + | + | +++ | ND | ++ | + |
| 89-76 | + | + | +++ | +++ | ND | +++ |
| 89-79 | + | ++ | +++ | +++ | +++ | ND |

The intensity of staining and the percentage of positive cells are represented by the + symbol (++++ = MI > 200; +++ = MI > 125; ++ = MI > 50; + = MI > 25; – = no staining above background). ND = not determined.

All antibodies blocked the binding of CD40Ig to activated human PBLs. However, the data shown in Table 4 clearly demonstrate the failure of some antibodies to block the binding of other antibodies to activated human PBLs, suggesting that they recognize distinct epitopes on the human gp39 molecules.

The 89-76 and 24-31 hybridomas, producing the 89-76 and 24-31 antibodies, respectively, were deposited under the provisions of the Budapest Treaty with the American Type Culture Collection, Parklawn Drive, Rockville, Md., on Sep. 2, 1994. The 89-76 hybridoma was assigned ATCC Accession Number HB 11713 and the 24-31 hybridoma was assigned ATCC Accession Number HB11712. The 24-31 and 89-76 antibodies are of the IgG1 isotype.

Experiment 3—Antibodies directed against mouse gp39

In one embodiment of the invention, the gp39 antagonist is an anti-mouse gp39 monoclonal antibody, MR1. The following method was used to produce the MR1 monoclonal antibody, and may be used to generate other antibodies directed toward gp39.

Hamsters were immunized intraperitoneally with 5–10$^6$ activated T$_h$1 cells (d1.6) at weekly intervals for six weeks. When the serum titer against murine T$_h$1 was greater than about 1:10,000, cell fusions were performed with polyethylene glycol using immune hamster splenocytes and NS-1. Supernatant from wells containing growing hybridomas were screened by flow cytometry on resting and activated T$_h$1. One particular hybridoma, which produced a Mab that selectively recognized activated T$_h$ was further tested and subcloned to derive MR1. MR1 was produced in ascites and purified by ion exchange HPLC. A hybridoma MR1 has been deposited with the American Type Culture Collection and assigned Accession Number HB11048.

EXAMPLE 7

Anti-human gp39 Antibodies can Inhibit Antibody and Xenoreactive T Cell Responses In this example, the effects of antibodies reactive against human gp39 on B and T cell reponses were investigated in hu-PBL-scid mice, an in vivo model of the human immune system.

Experiment 1—Anti-human gp39 blocks in vivo Tetanus toxoid specific antibody production in SCID mice reconstituted with human PBL Experiments presented above demonstrated that blockade of gp39 function inhibited T cell dependent polyclonal Ig production by human B cells in vitro (Table 3). To determine whether anti-hgp39 mAb could also inhibit antigen specific B cell antibody production in vivo, anti-gp39 antibody was adminstered to SCID mice reconstituted with human PBL (C.B-17-scid/scid mice).

C.B-17-scid/scid mice were injected intraperitoneally with 20×10$^6$ human PBL, immunized with 0.25 ml tetanus toxid (TT), and treated with PBS (250 µl) or anti-hgp39 (250 µg/d, twice weekly) and the secondary (IgG) anti-TT antibody response was assessed. Human anti-TT antibody levels were assessed by antigen-specific ELISA from sera collected weekly. Briefly, polyvinyl microtiter plates were coated with 5 Lf units/ml TT and incubated for 2 hr at 37° C. Plates were washed and subsequently incubated for an additional 2 hr with sera samples. A polyclonal goat mouse anti-human IgG (Fab)-alkaline phosphatase antibody used for detection of TT specific human Ig was added after washing. Plates were incubated an additional 2 hr at 37° C., developed by reaction with alkaline-phosphatase substrate and the O.D. at 410 nm determined based on multiple point analysis of sera samples diluted from 1:10–1:10,000. All mice with serum levels of human anti-tetanus toxoid antibody >0.100 O.D. at a 1:10 dilution were considered positive. Only positive mice were used in the calculation of the mean±SE values included in the table. The level of human anti-tetanus toxoid in sera from pre-immune mice or mice not immunized with tetanus toxoid was <0.02 O.D. Data are presented as mean±SE.

The results are presented in Table 5.

TABLE 5

| Recipient | | Anti-Tetanus Antibody (O.D. ± SE) (Frequency of Mice Containing Anti-Tetanus Antibody) days post immunization | | | |
|---|---|---|---|---|---|
| Strain | Treatment | 7 d | 14 d | 21 d | 28 d |
| C.B-17 scid/ | PBS | <0.02 (0/10) | .230 ± .042 (7/10) | .224 ± .040 (8/10) | .137 + .007 (4/10) |

TABLE 5-continued

| Recipient | | Anti-Tetanus Antibody (O.D. ± SE) (Frequency of Mice Containing Anti-Tetanus Antibody) days post immunization | | | |
|---|---|---|---|---|---|
| Strain | Treatment | 7 d | 14 d | 21 d | 28 d |
| scid | anti-hgp39 | .162 (1/10) | <0.02 (0/10) | <0.02 (0/10) | <0.02 (0/10) |

Immunization of hu-PBL-scid with TT resulted in detectable levels of IgG anti-TT antibody within 14 days post immunization in most animals. However, treatment with anti-hgp39 (24-31; 250 µg/day, twice weekly) completely ablated the secondary anti-TT antibody response in 9/10 mice examined, demonstrating that in vivo blockade of gp39 function also resulted in inhibition of antigen specific humoral responses.

Experiment 2—Anti-hgp39 treatment inhibits xenoreactive T cell responses

To determine whether anti-hgp39 antibody has an effect on xenoreactive T cell responses, hu-PBL-scid mice were treated with anti-hgp39 antibody and the number of engrafted cells was determined. In this model system of the human immune system, engraftment of T cells in the mice is generally a measure of xenoreactive T cell expansion.

NOD/LtSz-scid/scid mice were injected with 20×10$^6$ human PBL and further treated with anti-hgp39 antibody at 250 µg per injection twice weekly for 4 weeks or with PBS. Engraftment was assessed four weeks later by flow cytometric analysis of human CD45$^+$ cells in the spleens of recipient mice. NOD/LtSz-scid/scid mice were chosen as the recipient strain for these experiments as human PBL engraft at low levels in untreated C.B-17-scid/scid mice.

The results are summarized in Table 6.

TABLE 6

| Recipient Strain | Human Cell Source | Treatment | % of CD45+ Human Cells in Spleen of Recipient Mice | Frequency of Engrafted Mice (>8% CD45+) |
|---|---|---|---|---|
| NOD/LtSz-scid/scid | PBL | PBS | 12.7 ± 4.3 | 5/10 |
| | PBL | anti-hgp39 | <2.0 | 0/10 |
| NOD/LtSz-scid/scid | spleen | PBS | 32.6 ± 14.0 | 4/4 |
| | spleen | anti-hgp39 | 6.9 ± 0.8 | 3/10 |

The results demonstrate high engraftment of human PBL in 50% of control untreated NOD/LtSz-scid/scid recipient mice, with recipient mice containing >8% CD45$^+$ human cells. In contrast, none of the recipient mice treated with anti-hgp39 (0/10) contained >2% human CD45$^+$ cells. Similar results were obtained in experiments examining the engraftment of human spleen cells in NOD/LtSz-scid/scid mice (Table IV). When spleen cells were used as the source of donor human lymphocytes, a higher frequency of CD45$^+$ human cells was observed in the spleens of recipient mice (>8% in 4/4 mice). In addition, although treatment with anti-hgp39 significantly decreased the percent of CD45$^+$ cells in both spleen and blood of recipient mice, some engraftment was observed (>8% in 3/10 mice). Higher engraftment in scid mice which received human spleen cells was most likely due to the higher cell dose injected. The results indicate that, in both experiments, treatment with anti-hgp39 results in reduced engraftment of human lymphocytes in scid mice.

Thus, in vivo administration of anti-hgp39 antibody results in suppression of T cell reactivity to xenoantigen, and indicates that blockade of gp39 function can be utilized as an immunosuppressive agent for management of human allograft or xenograft rejection.

Experiment 3—Anti-hgp39 treatment does not inhibit antigen-specific T cell proliferative response of hu-PBL-scid spleen cells To determine whether treatment of hu-PBL-scid mice with anti-hgp39 altered the responsiveness of antigen-specific T cells in vivo, the proliferative response of spleen cells from hu-PBL-scid mice immunized with TT and treated with anti-hgp39 was assessed in vitro in secondary T cell response assays.

Spleen cells were obtained from TT immunized hu-PBL-scid mice four weeks after TT immunization and in vivo treatment with PBS (250 µl) or anti-hgp39 (250 µg/d, twice weekly). Spleen cells were cultured for 6 days in 96 well microtiter plates at a concentration of $1 \times 10^5$ cells/ml in the presence of 2.5 or 5.0 µg/ml TT or medium alone. Cultures were pulsed with 50 µCi of $^3$H-thymidine for the final 24 hr of culture and harvested. Stimulation indices were calculated as follows: SI=cpm TT−cpm medium alone/cpm medium alone.

Table 7 summarizes the results.

TABLE 7

| Recipient Strain | Treatment | Frequency of Responding Mice |
|---|---|---|
| C.B-17 scid/scid | PBS | 3/10 |
|  | anti-hgp39 | 5/10 |
| NOD/LtSz-scid/scid | PBS | 5/10 |
|  | anti-hgp39 | 6/10 |

Hu-PBL-scid mice treated with anti-hgp39 responded similarly to in vitro stimulation with TT as did hu-PBL-scid mice which were untreated (5/10 vs. 3/10 responding mice). Experiments using NOD/LtSz-scid/scid mice as recipients yielded similar results (Table 7). Thus, anti-hgp39 treatment does not alter the anti-tetanus T cell proliferative response following engraftment of human PBL in C.B-17-scid/scid or NOD/LtSz-scid/scid mice immunized with tetanus toxoid, although anti-TT antibodies were undetectable in these mice. These data demonstrate that treatment with anti-hgp39 does not result in deletion or functional inactivation of antigen-specific T cells in hu-PBL-scid mice and support the contention that inhibition of TT specific antibody responses by anti-hgp39 is due to blockade of gp39\CD40 interactions and subsequent B cell responses rather than T cell inactivation.

In view of the preceding results, administration of anti-human gp39 antibodies does not inhibit T cell responses to a specific soluble antigen (e.g., TT), at least under the conditions tested, but does block xenoreactive T cell responses in a T cell transplant recipient. These results indicate that administration of anti-gp39 antibodies to a transplant recipient (e.g., a bone marrow transplant recipient) would likely block expansion of the T cells population that is allo- or xeno-reactive to host antigens, but likely would not block the responsiveness of the transplanted T cells to foreign antigen (e.g., environmental antigens).

EQUIVALENTS

Hybridoma cell lines which secrete the 24-31 and 89-76 antibodies were deposited on Sep. 2, 1994 in the American Type Culture Collection in Rockville, Md. and respectively accorded accession numbers HB11712 and HB11713. These deposits were made in accordance with the Budapest Treaty. Further, all restrictions as to the availability of these hybridoma cell lines will be irrevocably removed upon issuance of a patent to this application.

Those skilled in the art will recognize, or be able to ascertain using no more than routine experimentation, many equivalents to the specific embodiments of the invention described herein. Such equivalents are intended to be encompassed by the following claims. The contents of all references and published patent applications cited throughout this application are hereby incorporated by reference.

We claim:

1. An anti-human gp39 (CD40L) monoclonal antibody that binds the epitope recognized by a monoclonal antibody selected from the group consisting of 24-31 secreted by hybridoma 24-31 designated by ATCC Accession No. HB1712 and 89-76 secreted by hybridoma 89-76 designated by ATCC Accession No. HB1713.

2. The anti-human gp39 antibody of claim 1 which is 89-76 secreted by hybridoma 89-76 designated by ATCC Accession No. HB1713.

3. The anti-human gp39 antibody of claim 1 which is 24-31 secreted by hybridoma 24-31 designated by ATCC Accession No. HB1712.

4. A pharmaceutical composition containing an anti-human gp39 antibody according to claim 1 and a pharmaceutically acceptable carrier.

5. The pharmaceutical composition of claim 4 wherein the antibody contained therein is 89-76 secreted by hybridoma 89-76 designated by ATCC Accession No. HB1713.

6. The pharmaceutical composition of claim 4 wherein the antibody contained therein is 24-31 secreted by hybridoma 24-31 designated by ATCC Accession No. HB1712.

7. A hybridoma 89-76 designated by ATCC Accession No. HB11713.

8. A hybridoma 24-31 designated by ATCC Accession No. HB11712.

* * * * *

UNITED STATES PATENT AND TRADEMARK OFFICE
CERTIFICATE OF CORRECTION

| | | |
|---|---|---|
| PATENT NO. | : 5,747,037 | Page 1 of 2 |
| APPLICATION NO. | : 08/475847 | |
| DATED | : May 5, 1998 | |
| INVENTOR(S) | : Randolph J. Noelle et al. | |

It is certified that error appears in the above-identified patent and that said Letters Patent is hereby corrected as shown below:

In the Specification:

First Page Col. 1 (Other Publications), Line 1, Delete "(H2)" and insert -- (ED) --.

First Page Col. 1 (Other Publications), Line 1, Delete "Raveu" and insert -- Raven --.

First Page Col. 1 (Other Publications), Line 2, After "only." Insert -- * --.

In the Abstract, Line 6, please delete "ATTC" and insert -- ATCC --.

Column 2, Line 27, After "Eur. J" insert --.--.

Column 3, Lines 5-7 (Approx.), Delete "it's" and insert -- its --.

Column 3, Line 44-45, Delete "pharmacuetical" and insert -- pharmaceutical --.

Column 11, Line 33, Delete "pretreatment" and insert -- pre-treatment --.

Column 13, Line 67, Delete "exampes" and insert -- examples --.

Column 16, Line 42, Delete "treatement" and insert -- treatment --.

Column 17, Line 49 (Approx.) After "and the" delete "the".

Column 27, Line 25 (Approx.) After "PBL" insert --.--.

Column 27, Line 32, Delete "adminstered" and insert -- administered --.

Column 30, Line 31, please delete "HB1713" and insert -- HB11713 --.

Column 30, Line 34, please delete "HB1713" and insert -- HB11713 --.

Column 30, Line 37, please delete "HB1712" and insert -- HB11712 --.

Column 30, Line 43, please delete "HB1713" and insert -- HB 11713 --.

UNITED STATES PATENT AND TRADEMARK OFFICE
CERTIFICATE OF CORRECTION

PATENT NO. : 5,747,037
APPLICATION NO. : 08/475847
DATED : May 5, 1998
INVENTOR(S) : Randolph J. Noelle et al.

It is certified that error appears in the above-identified patent and that said Letters Patent is hereby corrected as shown below:

Column 30, Line 46, please delete "HB1712" and insert -- HB11712 --.

Signed and Sealed this

Twenty-fourth Day of October, 2006

JON W. DUDAS
*Director of the United States Patent and Trademark Office*